US008606529B2

(12) United States Patent
Boles et al.

(10) Patent No.: US 8,606,529 B2
(45) Date of Patent: Dec. 10, 2013

(54) HIGH-RESOLUTION MELTING ANALYSIS

(75) Inventors: Deborah Boles, Cary, NC (US); Kenton C. Hasson, Germantown, MD (US); Sami Kanderian, Germantown, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 13/429,911

(22) Filed: Mar. 26, 2012

(65) Prior Publication Data

US 2012/0239305 A1   Sep. 20, 2012

Related U.S. Application Data

(63) Continuation of application No. 12/258,098, filed on Oct. 24, 2008, now Pat. No. 8,145,433.

(60) Provisional application No. 60/982,570, filed on Oct. 25, 2007.

(51) Int. Cl.
*G06F 19/00* (2011.01)

(52) U.S. Cl.
USPC ............. 702/19; 435/6; 435/7.1; 435/7.9; 435/91.1; 435/91.2; 544/245; 544/334; 544/242; 544/152; 536/23.1; 536/24.3

(58) Field of Classification Search
USPC ............. 702/19; 435/6, 7.1, 7.9, 4, 7.4, 91.1, 435/91.2, 287.2, 283.1; 544/245, 276, 277, 544/334, 242, 152; 536/23.1, 24.3
See application file for complete search history.

(56) References Cited

U.S. PATENT DOCUMENTS

| | | | | |
|---|---|---|---|---|
| 6,174,670 B1* | 1/2001 | Wittwer et al. | | 435/6 |
| 6,569,627 B2* | 5/2003 | Wittwer et al. | | 435/6 |
| 7,122,321 B2* | 10/2006 | Pantoliano et al. | | 435/7.1 |
| 7,160,998 B2* | 1/2007 | Wittwer et al. | | 536/24.3 |
| 7,387,887 B2* | 6/2008 | Wittwer et al. | | 435/91.2 |
| 7,456,281 B2* | 11/2008 | Dujols | | 544/242 |
| 7,582,429 B2* | 9/2009 | Wittwer et al. | | 435/6 |
| 7,670,832 B2* | 3/2010 | Wittwer et al. | | 435/283.1 |
| 7,781,165 B2* | 8/2010 | Birkner et al. | | 435/6 |
| 7,803,551 B2* | 9/2010 | Wittwer et al. | | 435/6 |
| 7,838,235 B2* | 11/2010 | Caplin | | 435/6 |
| 7,910,720 B2* | 3/2011 | Ankenbauer et al. | | 536/24.33 |
| 2002/0168686 A1* | 11/2002 | Pantoliano et al. | | 435/7.1 |
| 2004/0069656 A1* | 4/2004 | Cobb | | 205/775 |
| 2004/0077026 A1* | 4/2004 | Buechler | | 435/7.9 |
| 2005/0118623 A1* | 6/2005 | Belousov et al. | | 435/6 |
| 2005/0181384 A1* | 8/2005 | Piunno et al. | | 435/6 |
| 2007/0020672 A1* | 1/2007 | Wittwer et al. | | 435/6 |
| 2007/0026421 A1* | 2/2007 | Sundberg et al. | | 435/6 |
| 2007/0161020 A1* | 7/2007 | Luo et al. | | 435/6 |
| 2009/0075269 A1* | 3/2009 | Caplin | | 435/6 |
| 2009/0258414 A1* | 10/2009 | Wittwer et al. | | 435/287.2 |
| 2009/0311673 A1* | 12/2009 | Wittwer et al. | | 435/6 |

* cited by examiner

*Primary Examiner* — Carol S Tsai
(74) *Attorney, Agent, or Firm* — Rothwell, Figg, Ernst & Manbeck, P.C.

(57) ABSTRACT

The application relates to methods and systems for analysis of dissociation behavior of nucleic acids and identification of nucleic acids. In one aspect, methods and systems are disclosed for identifying a nucleic acid in a sample including an unknown nucleic acid and for detecting a single nucleotide polymorphism in a nucleic acid in a sample. Methods and systems are also disclosed for identification of a nucleic acid in a biological sample including at least one unknown nucleic acid by fitting denaturation data including measurements of a quantifiable physical change of the sample at a plurality of independent sample property points to a function to determine an intrinsic physical value and to obtain an estimated physical change function, and identifying the nucleic acid in the biological sample by comparing the intrinsic physical value for at least one unknown nucleic acid to an intrinsic physical value for a known nucleic acid.

25 Claims, 13 Drawing Sheets

HIGH-RESOLUTION MELTING ANALYSIS

CROSS-REFERENCE TO RELATED APPLICATION

This application is a continuation of U.S. application Ser. No. 12/258,098, filed Oct. 24, 2008, which claims the benefit of U.S. Provisional Patent Application Ser. No. 60/982,570, filed on Oct. 25, 2007, which is incorporated herein by reference in its entirety.

BACKGROUND

1. Field of the Invention

The present invention relates to methods and systems for the analysis of the dissociation behavior of nucleic acids and the identification of nucleic acids. More specifically, embodiments of the present invention relate to methods and systems for the analysis of denaturation data of nucleic acids.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

PCR is a powerful technique for amplifying short sections of DNA. With PCR, one can quickly produce millions of copies of DNA starting from a single template DNA molecule. PCR includes a three phase temperature cycle of denaturation of DNA into single strands, annealing of primers to the denatured strands, and extension of the primers by a thermostable DNA polymerase enzyme. This cycle is repeated so that there are enough copies to be detected and analyzed. In principle, each cycle of PCR could double the number of copies. In practice, the multiplication achieved after each cycle is always less than 2. Furthermore, as PCR cycling continues, the buildup of amplified DNA products eventually ceases as the concentrations of required reactants diminish. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

Real-time PCR refers to a growing set of techniques in which one measures the buildup of amplified DNA products as the reaction progresses, typically once per PCR cycle. Monitoring the accumulation of products over time allows one to determine the efficiency of the reaction, as well as to estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification in microfluidic devices is usually accomplished in one of two methods. In the first method, the sample solution is loaded into the device and the temperature is cycled in time, much like a conventional PCR instrument. In the second method, the sample solution is pumped continuously through spatially varying temperature zones. See, e.g., Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Melt curve analysis is an important technique for analyzing nucleic acids. In some methods, a double stranded nucleic acid is denatured in the presence of a dye that indicates whether the two strands are bound or not. Examples of such indicator dyes include non-specific binding dyes such as SYBR® Green I, whose fluorescence efficiency depends strongly on whether it is bound to double stranded DNA. As the temperature of the mixture is raised, a reduction in fluorescence from the dye indicates that the nucleic acid molecule has melted, i.e., unzipped, partially or completely. Thus, by measuring the dye fluorescence as a function of temperature, information is gained regarding the length of the duplex, the GC content or even the exact sequence. See, e.g., Ririe et al. (*Anal Biochem* 245:154-160, 1997), Wittwer et al. (Clin Chem 49:853-860, 2003), Liew et al. (Clin Chem 50:1156-1164 (2004), Herrmann et al. (Clin Chem 52:494-503, 2006), Knapp et al. (U.S. Patent Application Publication No. 2002/0197630), Wittwer et al. (U.S. Patent Application Publication No. 2005/0233335), Wittwer et al. (U.S. Patent Application Publication No. 2006/0019253), Sundberg et al. (U.S. Patent Application Publication No. 2007/0026421) and Knight et al. (U.S. Patent Application Publication No. 2007/0231799).

Some nucleic acid assays require identification of a single nucleotide change where the difference in melting temperature ($T_m$) between the wild type nucleic acid and the mutant nucleic acid is less than, for example, 0.25° C. This level of temperature resolution is difficult, if not impossible, in standard 96 and 384 well plates. Decreasing the area of thermal analysis can improve the spatial temperature gradient, but there is still significant noise generated from the heating device used to linearly ramp the samples during a thermal melt. Accordingly, what are desired are methods and systems for high resolution melt analysis that are capable of more accurately discriminating thermal melt curves and obtaining DNA sequence information from these melting curves, especially where these thermal melt curves are differentiated by a small temperature range. Also desired are methods and systems for high resolution melt analysis that more accurately identify thermal melt curves that facilitate detection of sequence information for DNA that contain one or more peaks or mutations.

SUMMARY OF THE INVENTION

The present invention relates to methods and systems for the analysis of the dissociation behavior of nucleic acids and the identification of nucleic acids. More specifically, embodiments of the present invention relate to methods and systems for the analysis of denaturation data of nucleic acids.

In one aspect, the present invention provides a method for identifying a nucleic acid in a sample including at least one unknown nucleic acid. According to this aspect, the method comprises fitting denaturation data, which includes measurements of a quantifiable physical change P of the sample at a plurality of independent sample property points x, to a function P(x, Q) to determine an intrinsic physical value Q and to obtain an estimated physical change function, wherein the intrinsic physical value Q is an intrinsic physical value associated with the nucleic acid in the sample, and the quantifiable physical change P is associated with denaturation of a nucleic acid. The method further comprises identifying the nucleic acid in the biological sample by comparing the intrinsic physical value Q for at least one unknown nucleic acid to the intrinsic physical value Q for a known nucleic acid.

In one embodiment, the comparison of the intrinsic physical value Q for at least one unknown nucleic acid is made to an a priori distribution of the intrinsic physical value Q for a known nucleic acid to determine if the unknown nucleic acid and the known nucleic acid are identical. In another embodiment, Q is one or more fitting parameters Y, Z and W and the denaturation data is fit to one or more of these fitting parameters to determine one or more intrinsic physical values Y, Z and W. In an additional embodiment, one or more of the intrinsic physical values Y, Z and W are determined and compared. In a further embodiment, two or more of the intrinsic physical values Y, Z and W are determined and compared. In yet another embodiment, all of the intrinsic physical values Y, Z and W are determined and compared.

In one embodiment, the sample further includes a double-strand specific fluorescent dye. In another embodiment, the quantifiable physical change is fluorescence intensity. In a further embodiment, quantifiable physical change P is ultraviolet absorbance. In one embodiment, x is the sample temperature T, Y is the melting temperature $T_m$, Z is the van't Hoff enthalpy $\Delta H$ and W is the amplitude A. In some embodiments, Y and Z are determined and compared in the method of the invention.

In one embodiment, the fitting step includes fitting the denaturation data to a function P(x, Q) using a computer-implemented non-linear least squares algorithm. In another embodiment, the non-linear least squares algorithm determines the value of at least one fitting parameter, and the intrinsic physical value Q is a fitting parameter whose value is determined by the non-linear least squares algorithm.

In a further embodiment, the fitting step includes fitting the denaturation data to a function $P_1(x, Q)$ to obtain a first estimated physical change function in which the function $P_1(x, Q)$ describes the relationship of the quantifiable physical change of a sample containing one nucleic acid to the independent sample property x. In another embodiment, the method further comprises the steps of (i) fitting the denaturation data to a function $P_2(x, Q_1, Q_2)$ to obtain a second estimated physical change function, in which the function $P_2(x, Q_1, Q_2)$ describes the relationship of the quantifiable physical change of a sample containing 2 distinct nucleic acids to the independent sample property x of a sample containing 2 distinct nucleic acids, and (ii) quantifying the number of distinct nucleic acids in the sample by comparing the first and second estimated physical change functions with the denaturation data to determine if 1 or 2 distinct unknown nucleic acids are present in the sample. In another embodiment, the determining step includes determining a melting temperature $T_{m(1)}$ for a first unknown nucleic acid and determining a melting temperature $T_{m(2)}$ for a second unknown nucleic acid.

In another embodiment, the method further comprises the step of calculating the binding fraction $g_i$ of each nucleotide in the nucleic acid from the fit parameters. In a further embodiment, the method further comprises the steps of calculating the analytical derivative of the estimated physical change function dP/dx and displaying a plot of said derivative based on the fit parameters Q to the function P. In yet another embodiment, the independent sample property x is the sample temperature T and the intrinsic physical value Y is the melting temperature $T_m$. In one embodiment, the fitting step is performed by fitting the denaturation data to an equation of the form $$P(T, T_m) = B + \sum_{i=1}^{n} P_i, \quad \text{(Eq. 1)}$$

wherein $$P_i = 2A_i g_i e^{[-k(T-T_{m_i})]}, \quad \text{(Eq. 2)}$$

$$g_i = 1 + \frac{1}{4e^{\left[\frac{\Delta H_i}{R}\left(\frac{1}{T_{m_i}} - \frac{1}{T}\right)\right]}} - \sqrt{\left(1 + \frac{1}{4e^{\left[\frac{\Delta H_i}{R}\left(\frac{1}{T_{m_i}} - \frac{1}{T}\right)\right]}}\right)^2 - 1}, \quad \text{(Eq. 3)}$$

and wherein

B is the baseline measurement of the quantifiable physical property in absence of the sample, $A_i$ is the amplitude of the measurement of the quantifiable physical property of the ith nucleic acid present in the sample, $\Delta H_i$ is the van't Hoff enthalpy of denaturation of the ith nucleic acid present in the sample, $T_{m(i)}$ is the melting temperature of the ith nucleic acid present in the sample, and R is the universal gas constant.

In another embodiment, the method further comprises the step of generating denaturation data from the sample. In one embodiment, the denaturation data is thermal melt data. In another embodiment, the unknown nucleic acid is a nucleic acid containing a single nucleotide polymorphism.

In another aspect, the present invention provides a system for identifying a nucleic acid in a sample including at least one unknown nucleic acid. According to this aspect, the system comprises a fitting module capable of fitting denaturation data, including measurements of a quantifiable physical change P of the sample at a plurality of independent sample property points x, to a function P(x, Q) to determine an intrinsic physical value Q and to obtain an estimated physical change function, wherein the intrinsic physical value Q is an intrinsic physical value associated with the nucleic acid in the sample, and the quantifiable physical change P is associated with denaturation of a nucleic acid. The system further comprises an identification module capable of identifying the nucleic acid in the biological sample by comparing the intrinsic physical value Q for the unknown nucleic acid to the intrinsic physical value Q for a known nucleic acid to determine if the unknown nucleic acid and the known nucleic acid are identical.

In one embodiment, Q is one or more fitting parameters Y, Z and W and the denaturation data is fit to one or more of these fitting parameters to determine one or more intrinsic physical values Y, Z and W. In another embodiment, one or more of the intrinsic physical values Y, Z and W are determined and compared. In an additional embodiment, two or more of the intrinsic physical values Y, Z and W are determined and compared. In a further embodiment, all of the intrinsic physical values Y, Z and W are determined and compared. In one embodiment, x is the sample temperature T, Y is the melting temperature $T_m$, Z is the van't Hoff enthalpy $\Delta H$ and W is the amplitude A. In some embodiments, Y and Z are determined and compared in the method according to the invention.

In one embodiment, the fitting module is a computer containing instructions for performing a non-linear least squares algorithm. In another embodiment, the independent sample property x is the sample temperature T. In a further embodiment, the intrinsic physical value Y is the melting temperature $T_m$. In one embodiment, the computer containing instructions for performing a non-linear least squares algorithm further contains instructions for fitting the denaturation data to a function of the form $$P(T, T_m) = B + \sum_{i=1}^{n} P_i, \quad \text{(Eq. 1)}$$

wherein $$P_i = 2A_i g_i e^{[-k(T-T_{m_i})]}, \quad \text{(Eq. 2)}$$

$$g_i = 1 + \frac{1}{4e^{\left[\frac{\Delta H_i}{R}\left(\frac{1}{T_{m_i}} - \frac{1}{T}\right)\right]}} - \sqrt{\left(1 + \frac{1}{4e^{\left[\frac{\Delta H_i}{R}\left(\frac{1}{T_{m_i}} - \frac{1}{T}\right)\right]}}\right)^2 - 1}, \quad \text{(Eq. 3)}$$

and wherein

B is the baseline measurement of the quantifiable physical property in absence of the sample, $A_i$ is the amplitude of the measurement of the quantifiable physical property of the ith nucleic acid present in the sample, $\Delta H_i$ is the van't Hoff enthalpy of denaturation of the ith nucleic acid present in the sample, $T_{m(i)}$ is the melting temperature of the ith nucleic acid present in the sample, and R is the universal gas constant.

In one embodiment, the fitting module includes a computer containing instructions for performing a non-linear least squares algorithm to determine the value of at least one fitting parameter, in which the melting temperature $T_m$ is a fitting parameter whose value is capable of being determined by the non-linear least squares algorithm. In another embodiment, the system further comprises a generating unit capable of generating denaturation data from the sample. In one embodiment, the denaturation data is thermal melt data.

In another aspect, the present invention provides a method for quantifying the number of distinct nucleic acids in a sample which includes at least one nucleic acid. In accordance with this aspect, the method comprises fitting denaturation data, including measurements of a quantifiable physical change P of the sample at a plurality of independent sample property points x, to a function $P_n(x)$ to obtain a first estimated physical change function, wherein said function $P_n(x)$ describes the relationship of the quantifiable physical change of a sample containing n distinct nucleic acids to an independent sample property x of a sample containing n distinct nucleic acids, and the quantifiable physical change P is associated with the denaturation of a nucleic acid. The method further comprises fitting the denaturation data to a function $P_{n+1}(x)$ to obtain a second estimated physical change function, wherein said function $P_{n+1}(x)$ describes the relationship of the quantifiable physical change of a sample containing n+1 distinct nucleic acids to an independent sample property x of a sample containing n+1 distinct nucleic acids. The method also comprises quantifying the number of distinct nucleic acids in the sample by comparing the first and second estimated physical change functions with the denaturation data to determine if n or n+1 different nucleic acids are present in the sample.

In one embodiment, the first fitting step includes determining the intrinsic physical value $Q_1$ for at least one of the nucleic acids present in the sample, and wherein the second fitting step includes determining an intrinsic physical value $Q_2$ for at least one of the nucleic acids in the sample. In another embodiment, the first fitting step includes fitting the denaturation data to a function $P_n(x)$ using a computer-implemented fitting algorithm, and the second fitting step includes fitting the denaturation data to a function $P_{n+1}(x)$ using a computer-implemented fitting algorithm. In a further embodiment, the independent sample property is the sample temperature T. In one embodiment, the computer-implemented fitting algorithms are non-linear least squares algorithms. In another embodiment, the non-linear least squares algorithm determines the value of at least one fitting parameter, in which the melting temperature $T_m$ of at least one nucleic acid is a fitting parameter whose value is determined by the non-linear least squares algorithm. In a further embodiment, the method further comprises the step of generating denaturation data from the sample. In one embodiment, the denaturation data is thermal melt data.

In another aspect, the present invention provides a system for quantifying the number of distinct nucleic acids in a sample which includes at least one nucleic acid. In accordance with this aspect, the system comprises a fitting module capable of fitting denaturation data, including measurements of a quantifiable physical change P of the sample at a plurality of independent sample property points x, to a function $P_n(x)$ to obtain an n nucleic acid estimated physical change function, wherein said function $P_n(x)$ describes the relationship of the quantifiable physical change of a sample containing n distinct nucleic acids to the independent sample property of a sample containing n distinct nucleic acids, and the quantifiable physical change is associated with the denaturation of a nucleic acid. The system further comprises a quantification module capable of quantifying the number of distinct nucleic acids in the sample by comparing an n nucleic acid physical change function and an n+1 nucleic acid physical change function with the denaturation data to determine if n or n+1 different nucleic acids are present in the sample.

In one embodiment, the independent sample property x is the sample temperature T. In another embodiment, the fitting module is capable of estimating the melting temperature $T_m$ for at least one of the nucleic acids present in the sample, in which the fitting module performs an estimation of the melting temperature $T_m$ for at least one of the nucleic acids in the sample. In a further embodiment, the fitting module is a computer containing instructions for fitting the denaturation data to a function $P_n(T)$ via a non-linear least squares algorithm. In one embodiment, the non-linear least squares algorithm is capable of determining the value of at least one fitting parameter, in which the melting temperature $T_m$ of at least one nucleic acid is a fitting parameter whose value is capable of being determined by the non-linear least squares algorithm. In another embodiment, the system further comprises a generating unit capable of generating denaturation data from the sample. In one embodiment, the denaturation data is thermal melt data.

BRIEF DESCRIPTION OF THE FIGURES

The accompanying drawings, which are incorporated herein and form part of the specification, illustrate various embodiments of the present invention.

DETAILED DESCRIPTION OF PREFERRED EMBODIMENTS

Figure 1:
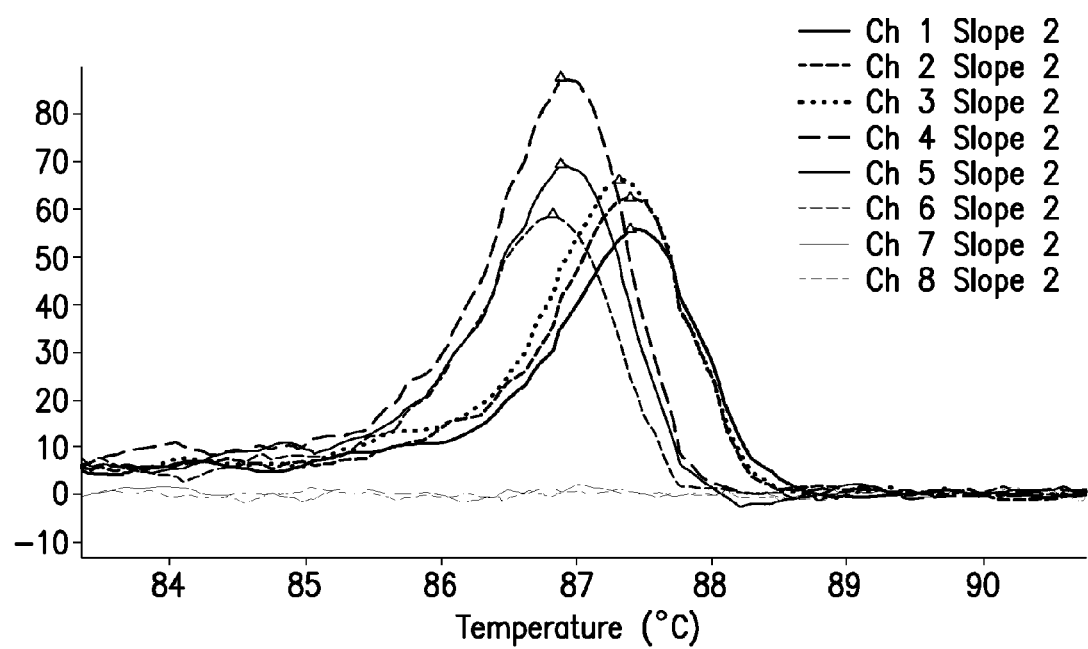
FIG. 1 illustrates a Savitsky-Golay derivative curve plot for a wild type and single nucleotide mutant nucleic acid.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

Thermal melt curves of fluorescence have been used to determine the melting temperature of a DNA strand when denatured from the duplex state to the two separate single strands via a ramp increase in temperature. Typically, the melting temperature or $T_m$ is defined to be the temperature at which 50% of the paired DNA strands have denatured into single strands. Intercalating dyes that fluoresce when bound to double stranded DNA and lose their fluorescence when denatured are often used in measuring $T_m$. Typically, the negative derivative of fluorescence with respect to temperature (−dF/dT) has been used in the determination of $T_m$. In typical systems, the temperature at the peak −dF/dT is used as an estimate of the melting temperature $T_m$.

The −dF/dT derivative curve is typically obtained using a Savitsky-Golay (SG) derivative filter which is capable of estimating the derivative of any signal. Savitsky-Golay filters are low pass, Finite Impulse Response (FIR) derivative filters, and their application to any dynamical signal is obtained through the convolution of the FIR filter parameters with the raw signal. When the spacing of the independent variable is uniform, the filtered results can give first order and higher order derivatives of the dependant variable relative to the independent variable equivalent. The effect of such a filter is equivalent to a moving polynomial fit, followed by the evaluation of the derivative of that polynomial evaluated at the center of the window. To use the SG filter the temperature difference between consecutive points has to be exactly equal (perfect ramp in temperature), otherwise there are potential problems, such as the lowering and broadening of peaks, due to the low pass filtering effect of the SG filter. Furthermore, the degree of filtering depends on the polynomial order and window size (or number of points). In the frequency domain, sharper peaks are further attenuated than broader ones. Perhaps the greatest shortcoming of the SG derivative filter is its inability to resolve and detect multiple melting temperatures for heterozygous mutant DNA when there are two or more $T_m$ temperatures that are in close proximity. In one aspect of the present invention, methods and systems are described that do not suffer from the shortcomings of using SG derivative filters and that have the ability to detect one or more melting temperature(s) from DNA thermal melt data as well as other thermodynamic parameters for each melting temperature.

In addition, when the melting temperatures between the wild type nucleic acid and the mutant nucleic acid are close enough, an overlap will be formed between two derivative melting curves, e.g., the derivative melting curves that are obtained for the wild type allele and the mutant allele in a heterozygous sample. Such an overlap in the derivative melting curves can effect the measurement of the melting temperature. In other aspects of the present invention, methods and systems are described that resolve the melting curves to precisely measure the melting temperatures of the alleles present in the sample.

The present invention relates to methods and systems for the analysis of the dissociation behavior of nucleic acids and the identification of nucleic acids. More specifically, the present invention relates to methods and systems for the analysis of denaturation data of nucleic acids and the identification of nucleic acids. For example, melting curve analysis can be used to detect single nucleotide polymorphisms (SNPs). Molecular melt curves (and differences between molecular melt curves) can also be used to detect and analyze sequence differences between nucleic acids. The thermal denaturation curve for nucleic acids can be monitored by, for example, measuring thermal parameters, fluorescence of indicator dyes/molecules, fluorescence polarization, dielectric properties, or the like.

Melting curve analysis is typically carried out either in a stopped flow format or in a continuous flow format. In one example of a stopped flow format, flow is stopped within a microchannel of a microfluidic device while the temperature in that channel is ramped through a range of temperatures required to generate the desired melt curve. In an alternative stopped flow format, melting curve analysis is done in a chamber to which the nucleic acid sample has been added. In one example of a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. An example of an instrument for performing a melting curve analysis is disclosed in U.S. Patent Application Publication No. 2007/0231799, incorporated herein by reference in its entirety.

The denaturation data that is analyzed in accordance with aspects of the present invention is obtained by techniques well known in the art. See, e.g., Knight et al. (U.S. Patent Application Publication No. 2007/0231799); Knapp et al. (U.S. Patent Application Publication No. 2002/0197630); Wittwer et al. (U.S. Patent Application Publication No. 2007/0020672); and Wittwer et al. (U.S. Pat. No. 6,174,670). Although the present invention is applicable to the analysis of denaturation data obtained in any environment, it is particularly useful for denaturation data obtained in the microfluidic environment because of the need for greater sensitivity in this environment.

In accordance with certain aspects of the invention, thermal melt data is generated by elevating the temperature of a molecule or molecules, e.g., of one or more nucleic acids, for a selected period of time and measuring a detectable property emanating from the molecule or molecules, wherein the detectable property indicates an extent of denaturation of the nucleic acid. This period of time can range, for example, from about 0.01 second through to about 1.0 minute or more, from about 0.01 second to about 10 seconds or more, or from about 0.1 second to about 1.0 second or more, including all time periods in between. In one embodiment, heating comprises elevating the temperature of the molecule or molecules by continuously increasing the temperature of the molecule or molecules. For example, the temperature of the molecule(s) can be continuously increased at a rate in the range of about 0.1° C./second to about 1° C./second. Alternatively, the temperature of the molecule(s) can be continuously increase at a slower rate, such as a rate in the range of about 0.01° C./second to about 0.1° C./second, or at a faster rate, such as a rate in the range of about 1° C./second to about 10° C./second. The heating can occur through application of an internal or an external heat source, as is known in the art.

The actual detection of a change(s) in a physical property of the molecules can be detected in numerous methods depending on the specific molecules and reactions involved. For example, the denaturation of the molecules can be tracked by following fluorescence or emitted light from molecules in the assay. The degree of, or change in, fluorescence is correlational or proportional to the degree of change in conformation of the molecules being assayed. Thus, in some methods, the detection of a property of the molecule(s) comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

In aspects of the present invention, the thermal melt data can be used to generate a thermal property curve. In some methods, the generation of a thermal property curve includes providing one molecule comprising a fluorescence indicator dye or fluorescence indicator molecule, and at least a second molecule comprising, one or more of an enzyme, a ligand, a peptide nucleic acid, a cofactor, a receptor, a substrate, a protein, a polypeptide, a nucleic acid (either double-stranded or single-stranded), an antibody, an antigen, or an enzyme complex. Fluorescence of the first molecule in the presence of the second molecule as a function of temperature is measured and the resulting data is used to generate a thermal property curve. In other methods, the generation of a thermal property curve comprises measuring a change in the fluorescence of one molecule that is correlative or proportional to a change in a physical property of another molecule(s) due to a change in temperature. In still other methods, the generation of a thermal property curve comprises measuring the change in the total free energy of the system as a function of temperature without the presence of a second molecule. Typically, the methods also include generating a thermal property curve of a control or known sample in a similar manner.

Several techniques exist for the measurement of the denaturation of the molecules of interest, and any of these can be used in generating the data to be analyzed in accordance with aspects of the present invention. Such techniques include fluorescence, fluorescence polarization, fluorescence resonance energy transfer, circular dichroism and UV absorbance. Briefly, the fluorescence techniques involves the use of spectroscopy to measure changes in fluorescence or light to track the denaturation/unfolding of the target molecule as the target molecule is subjected to changes in temperature. Spectrometry, e.g. via fluorescence, is a useful method of detecting thermally induced denaturation/unfolding of molecules. Many different methods involving fluorescence are available for detecting denaturation of molecules (e.g. intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

A method of measuring the degree of denaturation/unfolding of the target molecule is through monitoring of the fluorescence of dyes or molecules added to the microfluidic device along with the target molecule and any test molecules of interest. A fluorescence dye or molecule refers to any fluorescent molecule or compound (e.g., a fluorophore) which can bind to a target molecule either once the target molecule is unfolded or denatured or before the target molecule undergoes conformational change by, for example, denaturing and which emits fluorescent energy or light after it is excited by, for example, light of a specified wavelength.

One dye type used in the microfluidic devices is one that intercalates within strands of nucleic acids. The classic example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (*J Med Chem* 36(7):863-870 (1993)). The use of nucleic acid intercalating agents in measurement of denaturation is well known to those in the art. See, e.g., Haugland (*Handbook of Fluorescent Probes and Research Chemicals*, Molecular Probes, Inc., Eugene, Oreg. (1996)).

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (*Handbook of Fluorescent Probes and Research Chemicals*, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by Idaho Technology, Inc. (Salt Lake City, Utah, USA).

Fluorescence polarization (FP) provides a useful method to detect hybridization formation between molecules of interest. This method is especially applicable to hybridization detection between nucleic acids, for example, to monitor single nucleotide polymorphisms (SNPs). Generally, FP operates by monitoring, the speed of rotation of fluorescent labels, such as fluorescent dyes or molecular beacons, e.g. before, during, and/or after binding events between molecules that comprise the test and target molecules. In short, binding of a test molecule to the target molecule ordinarily results in a decrease in the speed of rotation of a bound label on one of the molecules, resulting in a change in FP.

Fluorescence resonance energy transfer (FRET) can be used to track the conformational changes of the target molecule (and interactions with test molecules which can bind with the target molecule) as a function of temperature. FRET relies on a distance-dependent transfer of energy from a donor fluorophore to an acceptor fluorophore. If an acceptor fluorophore is in close proximity to an excited donor fluorophore, then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate.

Circular dichroism (CD) can be used to follow the conformational changes of the target molecules/text molecules as a function of temperature and can be used to construct molecular melt curves. CD is a type of light absorption spectroscopy which measures the difference in absorbance by a molecule between right-circularly polarized light and left-circularly polarized light. CD is quite sensitive to the structure of polypeptides and proteins.

UV absorbance can also be used to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

Once the denaturation data has been obtained and melt curves generated, if desired, the data and/or melt curves are then analyzed to identify the molecules in the sample, such as, for example, the identification of a nucleic acid in a sample. This analysis is performed in accordance with the aspects of the present invention which are described herein.

In accordance with the certain aspects of invention, the original fluorescence data, that is, the raw fluorescence versus temperature data, is fitted directly to a model and then analyzed, without first applying a Savitsky-Golay (SG) filter to the data. In accordance with certain aspects of the invention, a model includes the temperature dependence of the fluorescence from the fluorophore used to generate the denaturation data. In accordance with certain aspects of the invention, the methods and systems can determine whether there is only one peak or more than one peak. Each of the aspects of the present invention can be implemented by a computer which would collect the data, analyze the data as in accordance with the methods described herein, and then provide a result of the analysis, which could include, for example, $T_m(s)$ of the nucleic acid(s) in the sample(s) and/or the identity of the nucleic acid(s) or SNP(s) in the sample(s).

FIG. 1 shows a negative derivative ($-dF/dT$) curve plot for a wild type and single nucleotide mutant nucleic acid associated with sickle cell anemia as obtained from an eight channel microfluidic device. The negative derivative curve plot is obtained from the fluorescence data using a Savitsky-Golay (SG) filter as known in the art. The $T_m$ is determined as the peak of the derivative curve and is reported in degrees Celsius. The delta $T_m$, or the difference in $T_m$'s between the two nucleic acids, is about 0.5° C. As the delta $T_m$ becomes smaller, it becomes increasing difficult to distinguish between two possible nucleic acids using the $T_m$ value alone.

Figure 2:
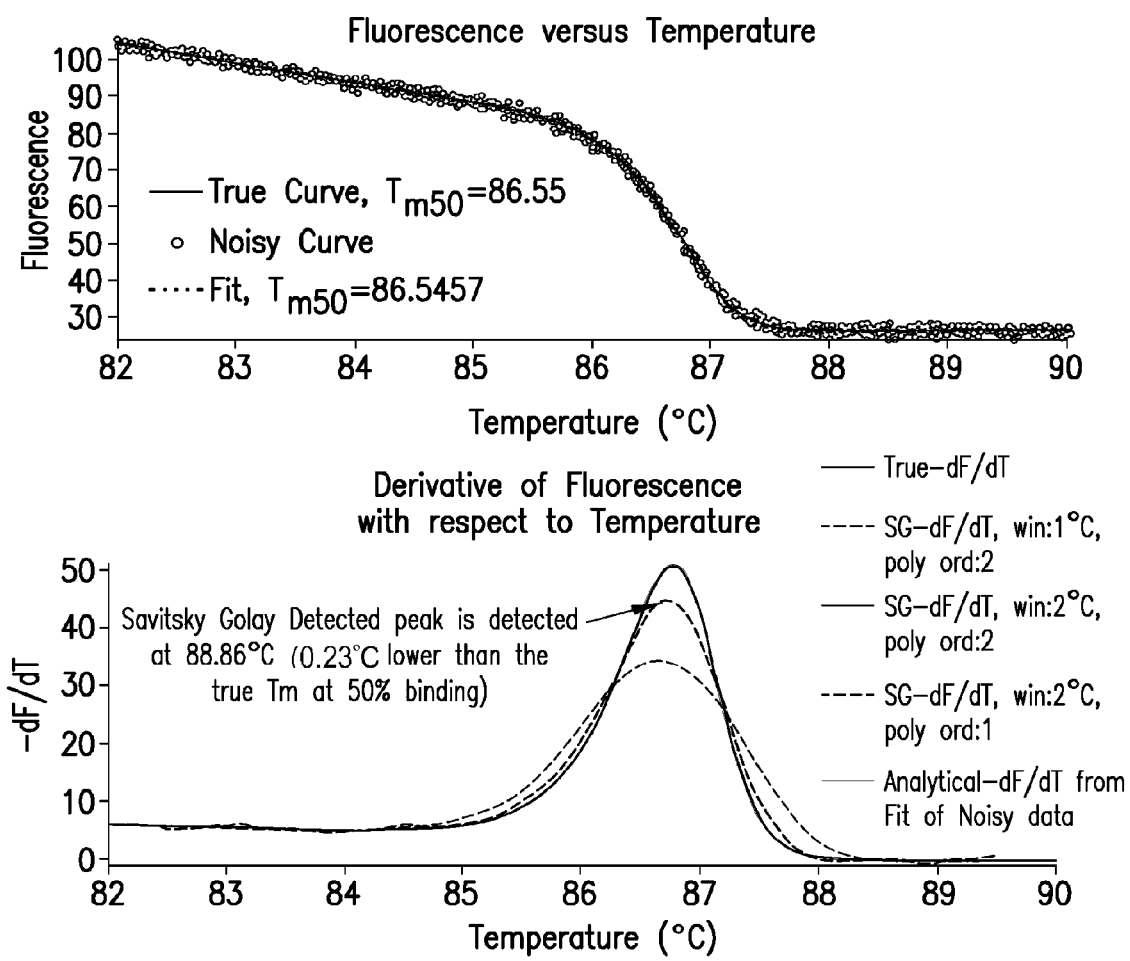
FIG. 2 illustrates the low pass filtering effect of the Savitsky-Golay filter.
Figure 3:
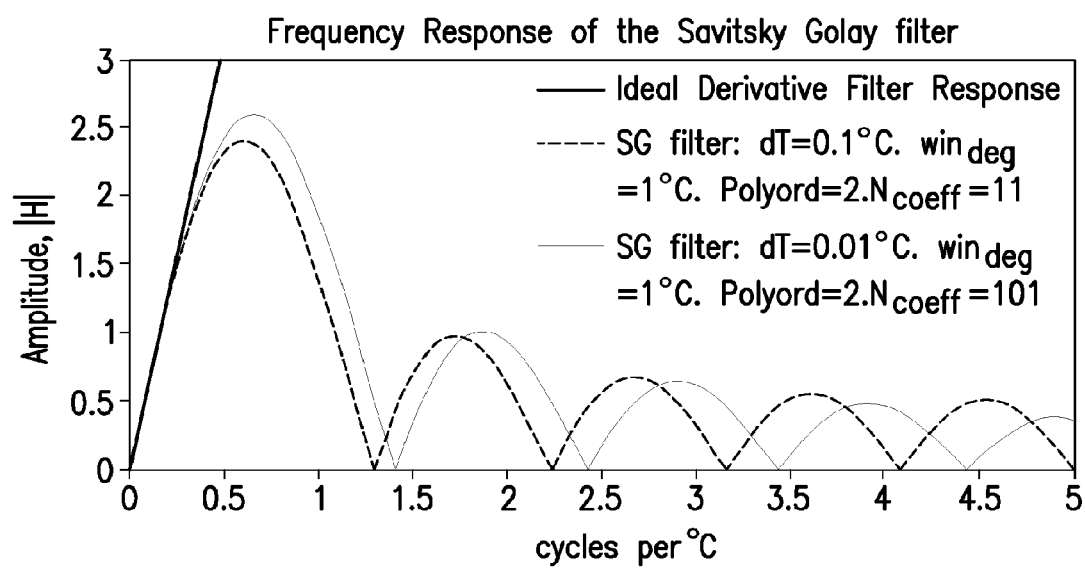
FIG. 3 illustrates that the amplitude frequency response of the Savitsky-Golay filter and that the attenuation of the −dF/dT curve.

In addition, problems arise with the use of SG filters in obtaining negative derivative curve data. FIG. 2 illustrates problems that can arise with the use of SG filters. In particular, FIG. 2 illustrates the simulation of a melting curve based on a mathematical model to determine the shape of a thermal melt curve in conjunction with its analytically derived derivative in the lower subplot. FIG. 2 shows that the low pass filtering effect of the Savitsky-Golay filter is dependant on the window size and polynomial order. The SG filter attenuates the true derivative signal. Also shown are various SG derivative plots based on different polynomial orders and window sizes. As shown, the low pass filtering effect of the SG filters lowers and broadens the peak. Furthermore, the degree of filtering depends on the polynomial order and window size (or number of points). In the frequency domain, it can also be shown that sharper peaks are further attenuated than broader ones, as shown by the amplitude-frequency response curve shown in FIG. 3. In particular, FIG. 3 shows that the attenuation of the −dF/dT curve caused by the SG filter is variable not only in the polynomial order and window size but also in the sharpness of the peak.

Figure 11:
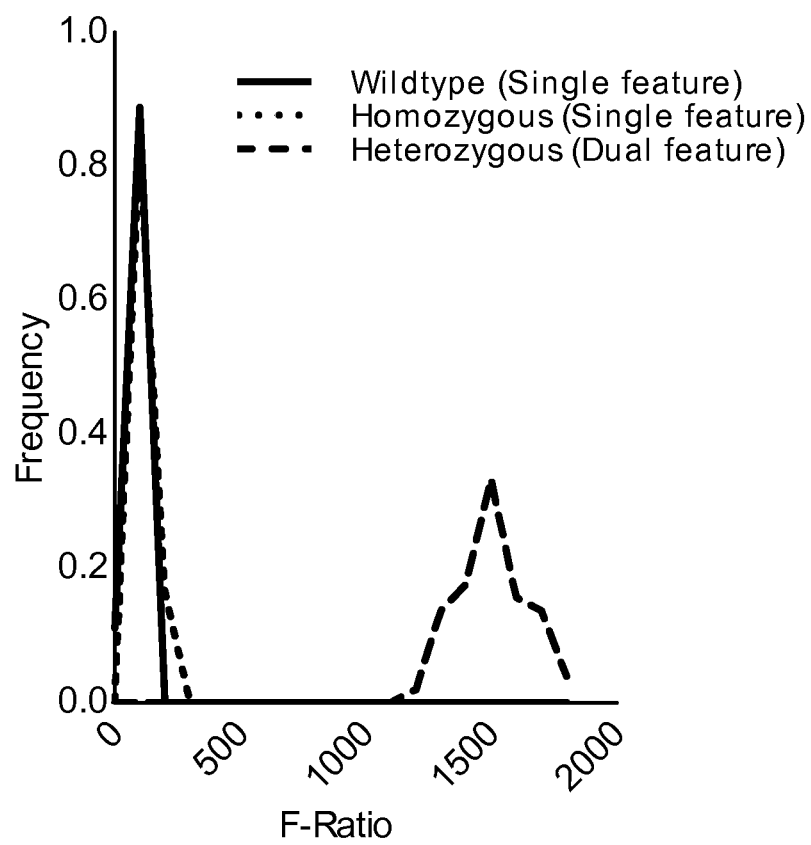
FIG. 11 illustrates the distribution of F-ratios for a group of melt curves of known genotypes for a particular assay and set of experimental conditions.

The true melting temperature of a nucleic acid is that where 50% of the paired nucleic acid exists in the unbound state due to the temperature increase ($T_m$ definition 1). It is important to note that the temperature at which the DNA unbinds at the maximal rate defined by the peak of the derivative curve ($T_m$ definition 2) is not the same as the temperature where 50% of the DNA is unbound. The method according to some aspects of the present invention can give the melting temperature as defined by either definition, as shown in FIG. 2. The method according to some aspects of the present invention does not require the derivation of −dF/dT to obtain $T_m$ according to definition 1. However it can derive the derivative curve if necessary and FIG. 11 shows that this yields a curve very close to the true derivative, unlike with the SG filters.

Figure 4:
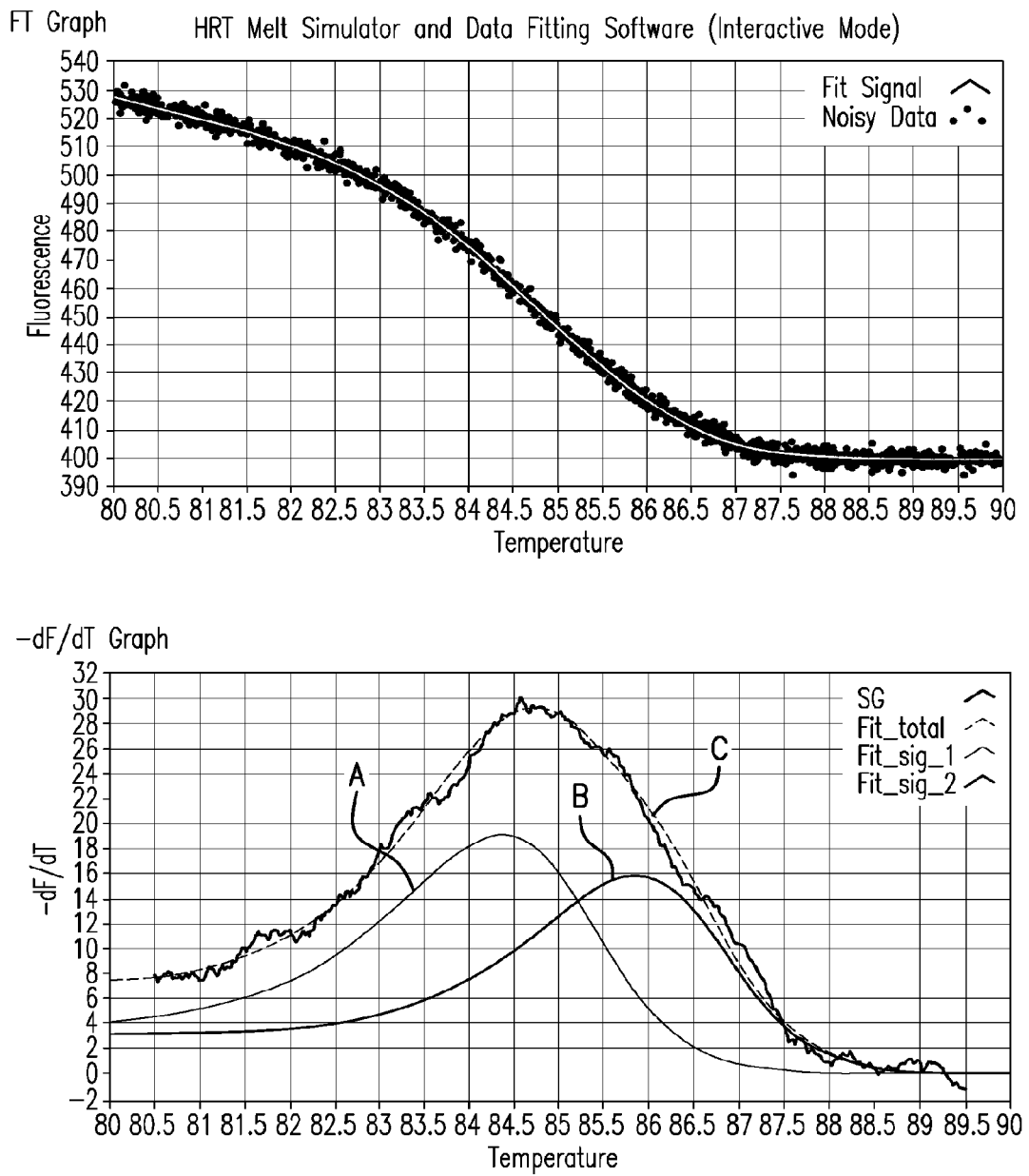
FIG. 4 illustrates a method of determining the presence of multiple nucleic acids in accordance with one aspect of the present invention.

Perhaps the greatest shortcoming of the SG derivative filter is its inability to resolve and detect multiple melting temperatures for heterozygous mutant DNA when there are two or more $T_m$ temperatures that are in close proximity. The method according to this aspect of the present invention has a much greater chance of overcoming this deficiency, as illustrated in FIG. 4. FIG. 4 shows that the method for determining melting temperatures according to one embodiment of the present invention is more successful at detecting the presence of two nucleic acids where their individual $T_m$s are close (such as, for example, within 1.5° C.) of each other. The total derivative which the Savitzky-Golay filter estimates can not detect the presence of two nucleotides when their melting temperatures are close.

In accordance with other aspects, the present invention provides methods and systems that utilize an algorithm that has the ability to detect one or more melting temperature(s) from nucleic acid thermal melt data as well as other thermodynamic parameters such as the enthalpy and amplitude (signal level) for each melting temperature. In one aspect, the methods and systems are based on fitting thermal melt data to a mathematical model through non-linear least squares fitting of parameters. But this algorithm does more than fit data to equations. It has the ability to adaptively expand the equation set to detect multiple features due to multiple mutations, but only if necessary. Based on this method, results yield more accurate information and more melting temperatures that are more robust than in connection with the SG method. Furthermore, the present methods produce a −dF/dT curve that is closer to the true curve, if such a curve is desired. In accordance with this aspect of the invention, the model assumes that the change in heat capacity is zero.

Each feature has a unique melting temperature $(Tm_i)_e$, enthalpy ($\Delta H_i$), florescence amplitude ($A_i$), a common decay constant (k) and fluorescence offset (B), each defined by the following equations.

Total Fluorescence Equation $$F_{sum} = B + \sum_{i=1}^{N_{pk}} F_i \qquad \text{Equation 1}$$

Fluorescence of Individual Features $$F_i = 2A_i g_i e^{[-k(T-T_{m_i})]} \qquad \text{Equation 2}$$

Binding Fraction of Individual Features $$g_i = 1 + \frac{1}{4e^{\left[\frac{\Delta H_i}{R}\left(\frac{1}{T_{m_i}} - \frac{1}{T}\right)\right]}} - \sqrt{\left(1 + \frac{1}{4e^{\left[\frac{\Delta H_i}{R}\left(\frac{1}{T_{m_i}} - \frac{1}{T}\right)\right]}}\right)^2 - 1} \qquad \text{Equation 3}$$

In the detection of one feature, the vector of parameter estimates is:

$$P = \begin{bmatrix} T_m \\ \Delta H \\ A \\ B \\ k \end{bmatrix}$$

In the detection of two features the vector of parameter estimates is:

$$P = \begin{bmatrix} T_{m1} \\ \Delta H_1 \\ A_1 \\ T_{m2} \\ \Delta H_2 \\ A_2 \\ B \\ k \end{bmatrix}$$

In general, the number of parameters in the detection of $N_{pk}$ features is equal to $3(N_{pk})+2$. For any number of features, the fluorescence melt data is fit to the mathematical model, such as described herein. In accordance with this aspect of the invention, this mathematical model assumes that the change in heat capacity is zero, and thus does need to be determined.

In one aspect, the present invention utilizes non-linear least squares fitting to identify melting temperatures and other useful parameters. The general form of any non-linear equation (regardless of the number of parameters) can be written as a function of the independent variable and the constant parameters that one wishes to solve for:

$$y = f(x, P_1, P_2, \ldots, P_m).$$

Thus the $i^{th}$ dependent variable in terms if the $i^{th}$ independent variable is of the form:

$$y_i = f(x_i, P_1, P_2, \ldots, P_m).$$

Unconstrained nonlinear least-squares data fitting by the Gauss-Newton or Marquardt-Levenberg method can be applied as follows:

1. Start with an initial estimation for each of the unknown parameters:

$$P = \begin{bmatrix} P_1 \\ P_2 \\ \vdots \\ P_m \end{bmatrix}.$$

2. For each temperature reading ($x_i$) value, using the current parameters in P, evaluate the estimated fluorescence value ($\hat{y}_i$):

$\hat{y}_i = f(x_i, P_1, P_2, \ldots, P_m)$. In vector form $$\hat{Y} = \begin{bmatrix} \hat{y}_1 \\ \hat{y}_2 \\ \vdots \\ \hat{y}_n \end{bmatrix},$$

if there are n pairs.

3. Compute the residual vector R, which is the difference between the measured fluorescence and estimated fluorescence:

$$R = \begin{bmatrix} r_1 \\ r_2 \\ \vdots \\ r_n \end{bmatrix} = \hat{F} - F = \begin{bmatrix} \hat{f}_1 \\ \hat{f}_2 \\ \vdots \\ \hat{f}_n \end{bmatrix} - \begin{bmatrix} f_1 \\ f_2 \\ \vdots \\ f_n \end{bmatrix}.$$

4. Compute the Sum of the Squared Errors scalar value for the current estimates:

$$SSE = \sum_{i=1}^{n} \left( \hat{f}_i - f_i \right)^2.$$

In matrix form, $SSE = R^T R$.

If the percent change in SSE from the proceeding value is less than or equal to some small tolerance value, such as, for example, 0.01%, then stop here and use the current parameters in P as the parameters that yield minimum SSE. For example:

If $\dfrac{SSE_{this\ iteration} - SSE_{last\ iteration}}{SSE_{this\ iteration}} \leq 10^{-4}$ then STOP.

5. Take an infinitesimal step, $\partial P$ away along the axis of each parameter in order to discretely calculate the local gradient or Jacobian:

$$\partial P = \begin{bmatrix} \partial P_1 \\ \partial P_2 \\ \vdots \\ \partial P_m \end{bmatrix} = \gamma \cdot P = \gamma \cdot \begin{bmatrix} P_1 \\ P_2 \\ \vdots \\ P_m \end{bmatrix} = \begin{bmatrix} \gamma P_1 \\ \gamma P_2 \\ \vdots \\ \gamma P_m \end{bmatrix},$$

where $\gamma$ is a very small scalar constant (on the order of approximately $10^{-8}$).

6. Compute the Jacobian (partial derivative) matrix of the function $f$ with respect to each parameter at the current estimate of the function, $\hat{\gamma}$ for each x value:

$$J = \begin{bmatrix} \dfrac{\partial \hat{y}_1}{\partial P_1} & \dfrac{\partial \hat{y}_1}{\partial P_2} & \cdots & \dfrac{\partial \hat{y}_1}{\partial P_m} \\ \dfrac{\partial \hat{y}_2}{\partial P_1} & \dfrac{\partial \hat{y}_2}{\partial P_2} & \cdots & \dfrac{\partial \hat{y}_2}{\partial P_m} \\ \vdots & \vdots & \ddots & \vdots \\ \dfrac{\partial \hat{y}_n}{\partial P_1} & \dfrac{\partial \hat{y}_n}{\partial P_2} & \cdots & \dfrac{\partial \hat{y}_n}{\partial P_m} \end{bmatrix},$$

where $\dfrac{\partial \hat{y}_i}{\partial P_1}$ is equated discretely as $$\dfrac{f(x_i, P_1 + \partial P_1, P_2, \ldots, P_m) - f(x_i, P_1, P_2, \ldots, P_m)}{\partial P_1}, \dfrac{\partial \hat{y}_i}{\partial P_2}$$

is equated discretely as $$\dfrac{f(x_i, P_1, P_2 + \partial P_2, \ldots, P_m) - f(x_i, P_1, P_2, \ldots, P_m)}{\partial P_2} \cdots \dfrac{\partial \hat{y}_i}{\partial P_n}$$

is equated discretely as $$\dfrac{f(x_i, P_1, P_2 + \partial P_2, \ldots, P_m) - f(x_i, P_1, P_2, \ldots, P_m)}{\partial P_n}.$$

7. Compute $\Delta P$ which is a step vector that is to be added to the current P vector in the next iteration as follows:

$\Delta P = pinv(J) * R = (J^T J)^{-1} J^T R$.

8. Generate a new vector of parameters:

$P = P + \Delta P$.

9. Repeat steps 2 through 8 until the percent change in SSE is less than or equal to the tolerance value in step 4, or until a maximum set amount of iterations have been performed, such as, for example, 100. In one embodiment, each time this loop is run, the number of iterations increments by 1. If the maximum number of iterations has been performed and the percent change in SSE is greater than the tolerance value, then the parameters did not converge to a local minimum.

Figure 5:
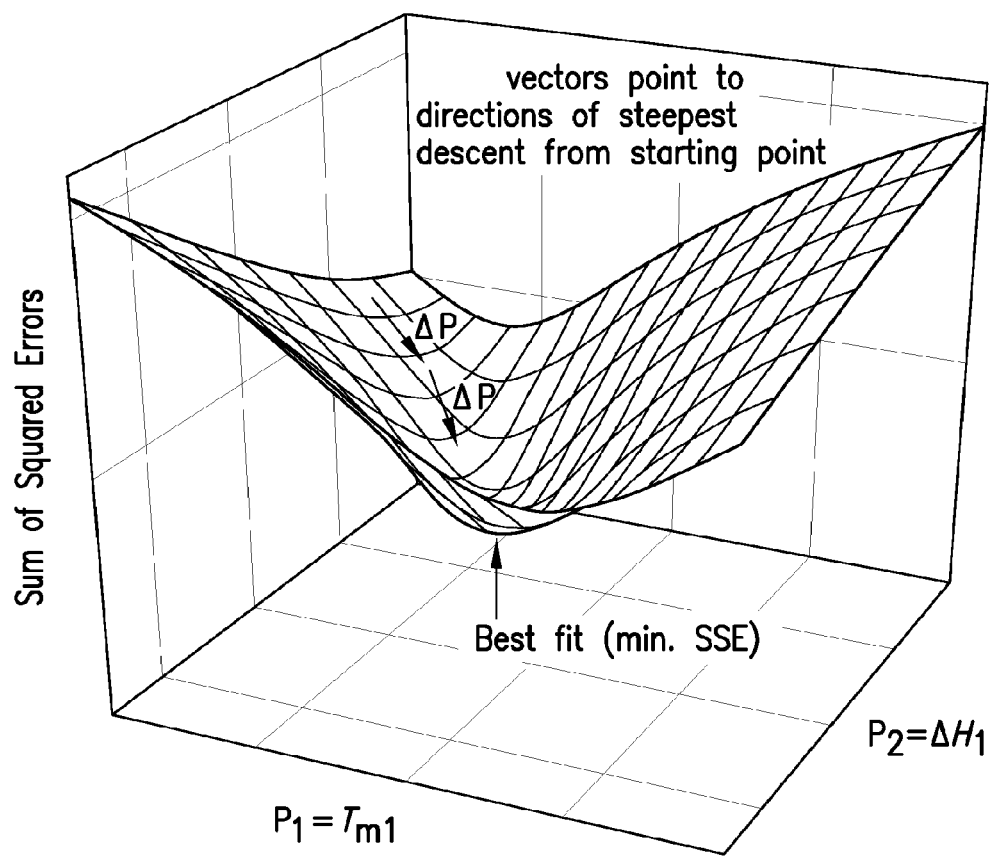
FIG. 5 shows a visual representation of iterative steepest descent algorithm with two unknown parameters, $P_1$ and $P_2$, in accordance with one aspect of the present invention.

An explanation of how the algorithm functions mathematically is explained in connection with the illustration in FIG. 5. FIG. 5 shows a visual representation of iterative steepest descent algorithm with two unknown parameters, $P_1$ and $P_2$ (e.g. Tm, $\Delta H$, etc. . . . ). The procedure is the same with more than two unknowns but is difficult to visualize as more than three dimensions are needed. Note that the number of unknowns for Npk peaks is 3*Npk+2. An initial estimation of the parameters ($P_1$, $P_2$) is located somewhere on the shaded surface shown in FIG. 5. From the current position (iteration), a new vector, $\Delta P$, is calculated whose magnitude and direction is influenced by the Jacobian matrix J, and the residual vector R. The vector $\Delta P$ points in the direction of steepest descent (slope) on the surface and results in the identification of a new point P. This procedure iteratively repeats until the surface is almost flat (tolerance is reached). This means that the local minimum point is largely obtained and the iteration process can be stopped. Of course, this technique is not limited to fitting equations 1 through 3.

In accordance with some aspects, the method includes estimating quality of the results by using the Jacobian matrix to estimate the Standard Error (or deviation) of each of the parameter estimates, and using residuals and parameter estimates to obtain SNR. Once the least squares set of parameters defined in vector P is obtained, the vector consisting of standard error (or deviation) of each parameter can be estimated. The covariance matrix of parameter estimates can be calculated as:

$$C = \frac{R^T R (J^T J)^{-1}}{n-m}$$

wherein

R and J are the residual vector and Jacobian matrix respectively which are defined above, n is the number of fluorescence-temperature data points included in the fit and m is the number of parameters that are fit.

The standard deviation of the estimated parameters can be equated as the square root of the diagonal elements of C:

$$STDP = \begin{bmatrix} \sqrt{C_{1,1}} \\ \sqrt{C_{2,2}} \\ \vdots \\ \sqrt{C_{m,m}} \end{bmatrix}.$$

The amount or standard deviation of noise can be equated as the standard deviation of the residual vector which is a scalar:

$$stdr = \sqrt{\frac{\sum_{k=1}^{n}(r_i - \bar{r})^2}{n-1}}.$$

The signal magnitude is determined by the fit parameter $A_i$ for each feature. A is the florescence level above the base fluorescence B, at the melting temperature $T_m$.

The signal to noise ratio for each feature, is quantified as:

$$SNR_i = \frac{A_i}{stdr}.$$

In accordance with aspects of the invention, an adaptive, intelligent determination of the number of features (1, 2 or 3 etc. . . . ) can be determined. In fitting the parameters to equations 1 through 3, it is desirable to know how many features or nucleotides there are to fit to the correct equation as i goes from 1 to $N_{pk}$.

Figure 6:
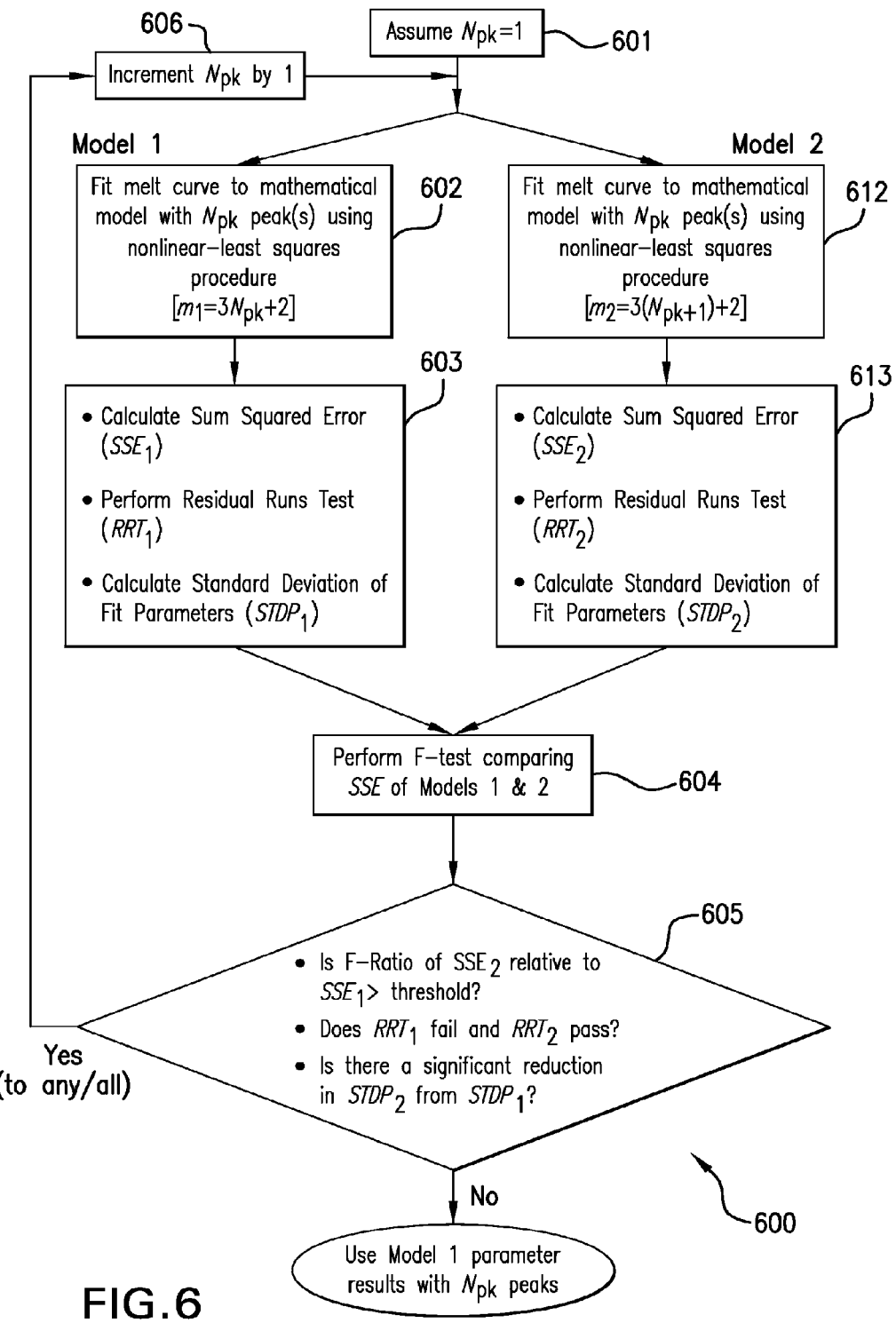
FIG. 6 illustrates a flow chart showing the adaptive procedure for determining model equations complexity (number of peaks or nucleotides) in accordance with one aspect of the present invention.

FIG. 6 illustrates a flow chart for a process 600 for an adaptive procedure for determining model equation complexity, i.e., number of peaks or nucleotides, in accordance with an embodiment of the present invention. Process 600 may begin in step 601 in which all melt curves are initially assumed to consist of 1 peak. The data is then fit twice, once assuming a mathematical model with 1 peak, and once assuming a model consisting of 2 peaks. Thus, in step 602, the melt curve is fit to a mathematical model with $N_{pk}$ peak(s) using nonlinear-least squares procedure [$m_1=3N_{pk}+2$.], while in step 612, the melt curve is fit to a mathematical model with $N_{pk}$ peak(s) using nonlinear-least squares procedure [$m_2=3(N_{pk+1})+2$]. In step 603, the Sum Squared Error ($SSE_1$) is calculated, the Residual Runs Test ($RRT_1$) is performed and the Standard Deviation of Fit Parameters ($STDP_1$) is calculated for the data from step 602, while in step 613, the Sum Squared Error ($SSE_2$) is calculated, the Residual Runs Test ($RRT_2$) is performed and the Standard Deviation of Fit Parameters ($STDP_2$) is calculated for the data from step 612.

In step 604, an F-test is performed comparing $SSE_1$ from step 603 and $SSE_2$ from step 613. In one embodiment, three queries of the data are made in step 605. First, is the F-ratio of $SSE_2$ relative to $SSE_1$ much greater than the predicted threshold? Second, does $RRT_1$ fail and $RRT_2$ pass? Third, is there a significant reduction in $STDP_2$ from $STDP_1$? If the answers to these queries are no, then the Model 1 parameter results with $N_{pk}$ peaks is used. If the answer is yes to any or all of the queries, then in step 606, $N_{pk}$ is incremented by one and the data is again fit to the two models by repeating the steps described above. In summary, if the fit results show a significant improvement with the added peak, then that more complex mathematical model is chosen over the simpler one.

In one embodiment, the threshold is determined by calculating the F-ratio of many melt curves of known nucleic acids, such as, for example, as illustrated in FIG. 11. It is known that the wild type and homozygous mutant nucleic acids have one feature and that the single heterozygous mutant has two features. Based on the F-ratio distributions of these nucleic acids, approximately 750 would be a good threshold in this example. The F-ratio distributions (and thus the threshold) may change for different assays and different experimental conditions, but can be pre-determined from a data set specific to those same conditions.

Because the model with the added peak is a superset of the simpler model, $SSE_2$ is always less that $SSE_1$. But it is desirable to know whether the improvement in SSE is worth the extra 3 parameters needed to describe the added feature. The F-test in step 604 is used to answer this question. The F-test for comparing a 1-peak model to a 2-peak model is given by the formula:

$$F_{ratio} = \frac{(SSE_1 - SSE_2)/(m_2 - m_1)}{SSE_2/(n - m_2)}$$

in which $m_1$ is the number of fit parameters for the 1-peak model which is 5, $m_2$ is the number of fit parameters for the 2-peak model which is 8 and n is the number of data points included in the fit. If the simpler model is correct, an F ratio near 1.0 would be expected. If the ratio is much greater than 1.0, then it is highly likely that the more complicated model is correct.

Figure 7A:
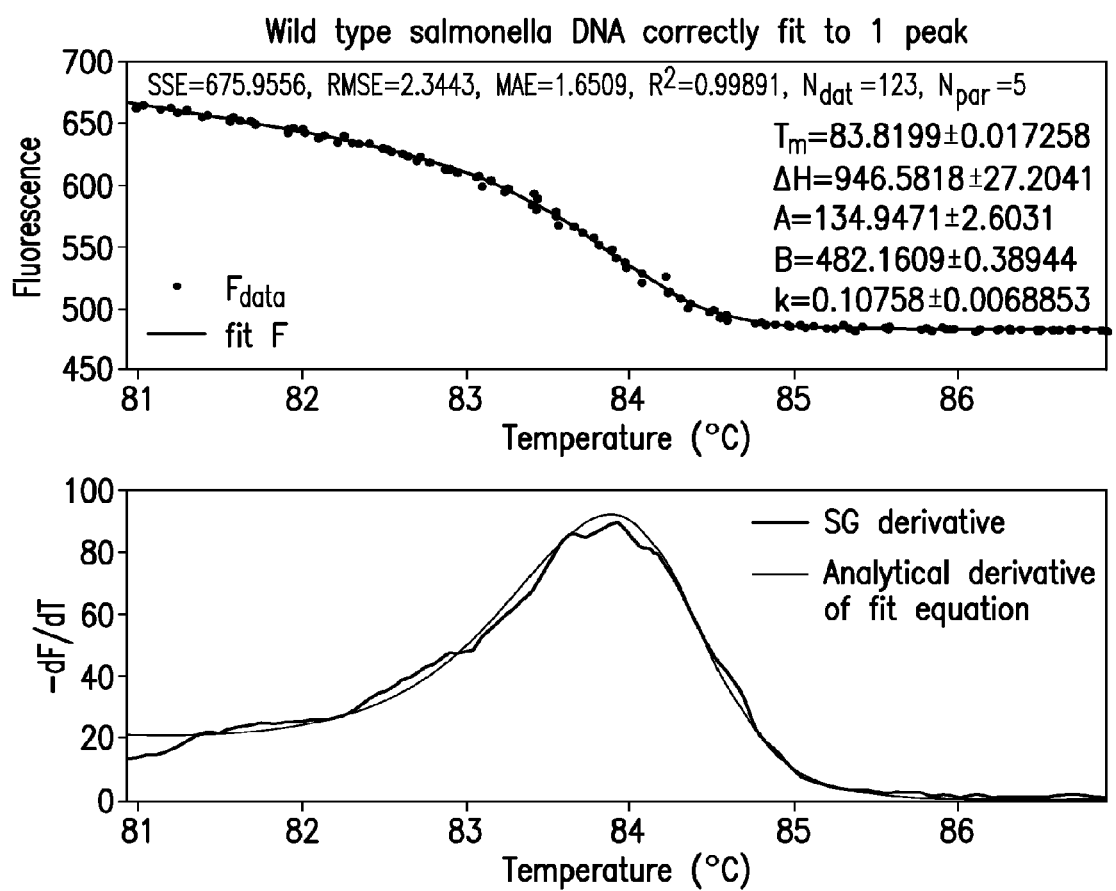
FIGS. 7A and 7B illustrate a method for describing a melt curve using a single peak in accordance with one aspect of the present invention obtained from wild type salmonella DNA. In this example, a single peak is adequate to describe this data as the F-ratio between the two peak model fit (7B) and one peak model fit (7A) is 2.45 which is relatively low.
Figure 7B:
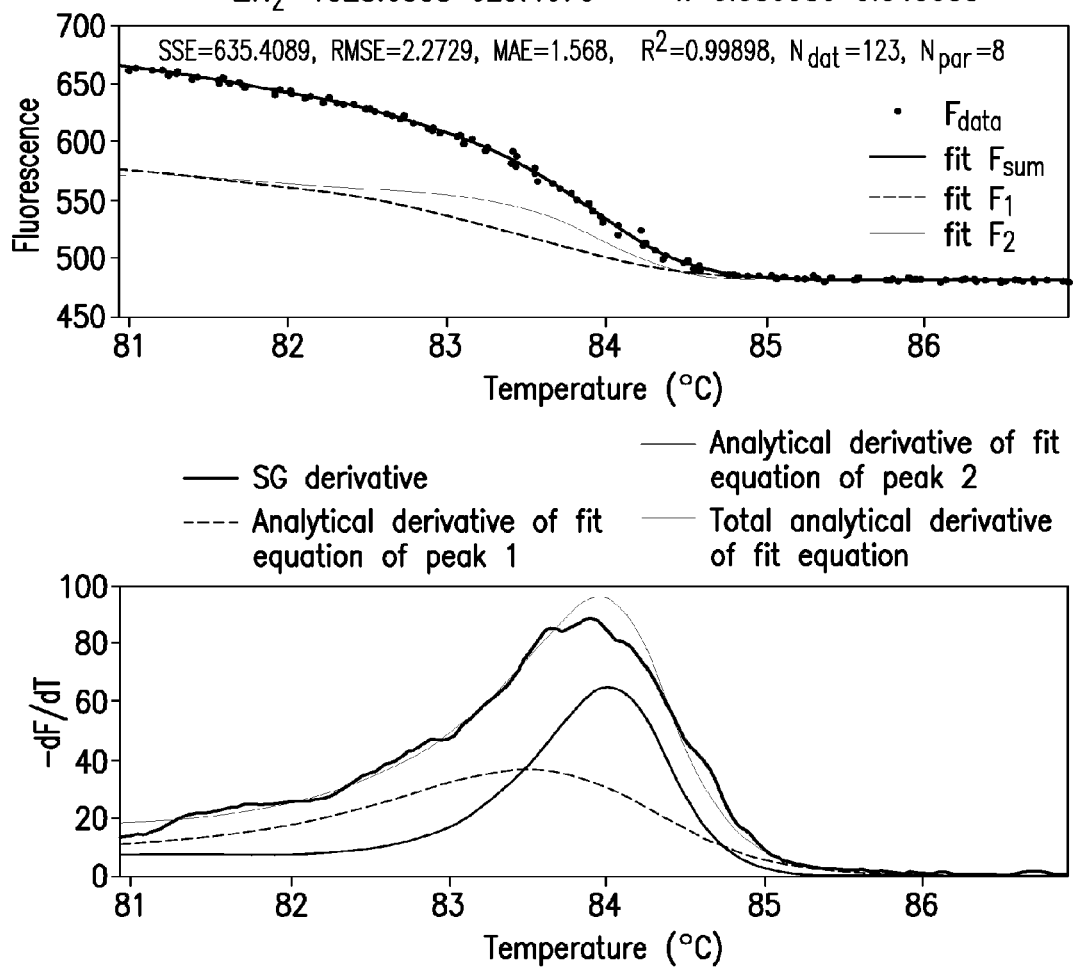
Figure 8A:
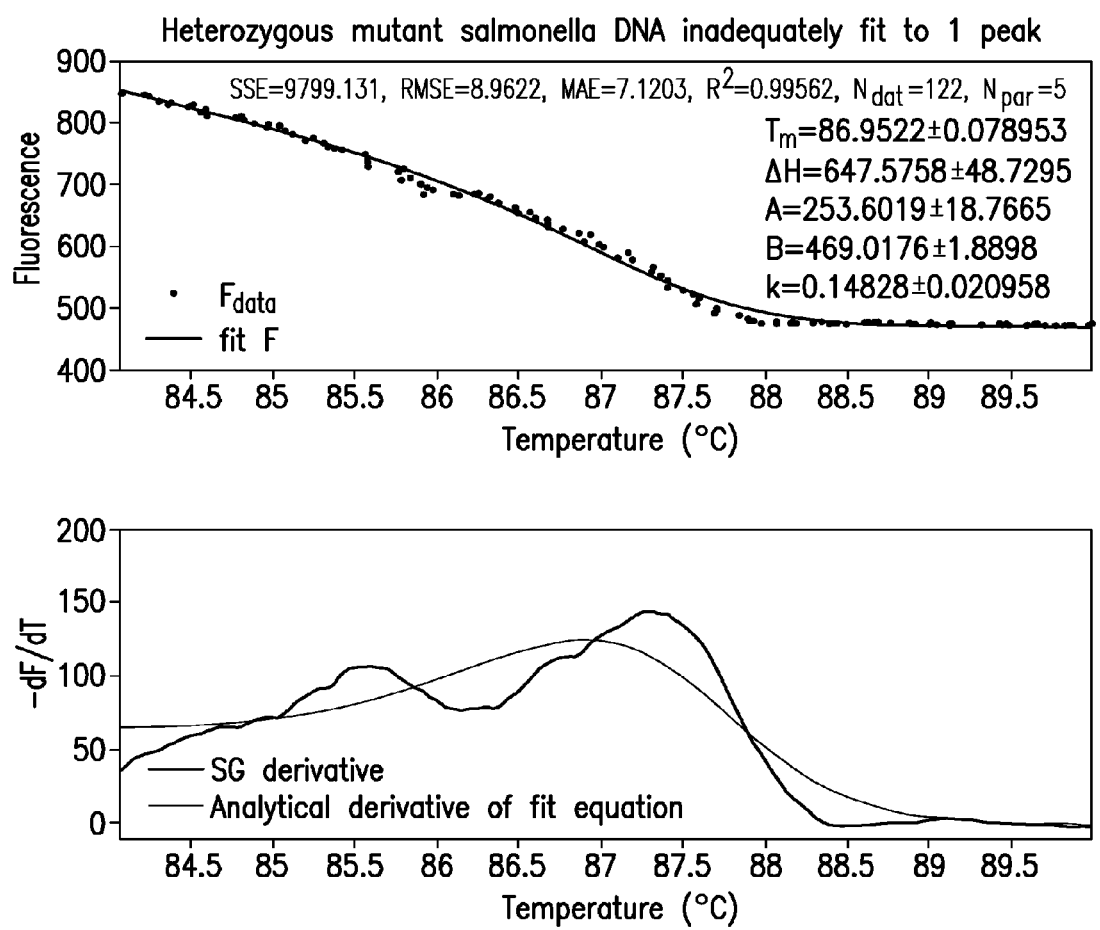
FIGS. 8A and 8B illustrate a method for describing a melt curve using two peaks in accordance with one embodiment of the present invention. In this example, two peaks (or nucleotides) are necessary to describe this data as the F-ratio between the two peak model fit (8B) and one peak model fit (8A) is 1500 which is relatively high.
Figure 8B:
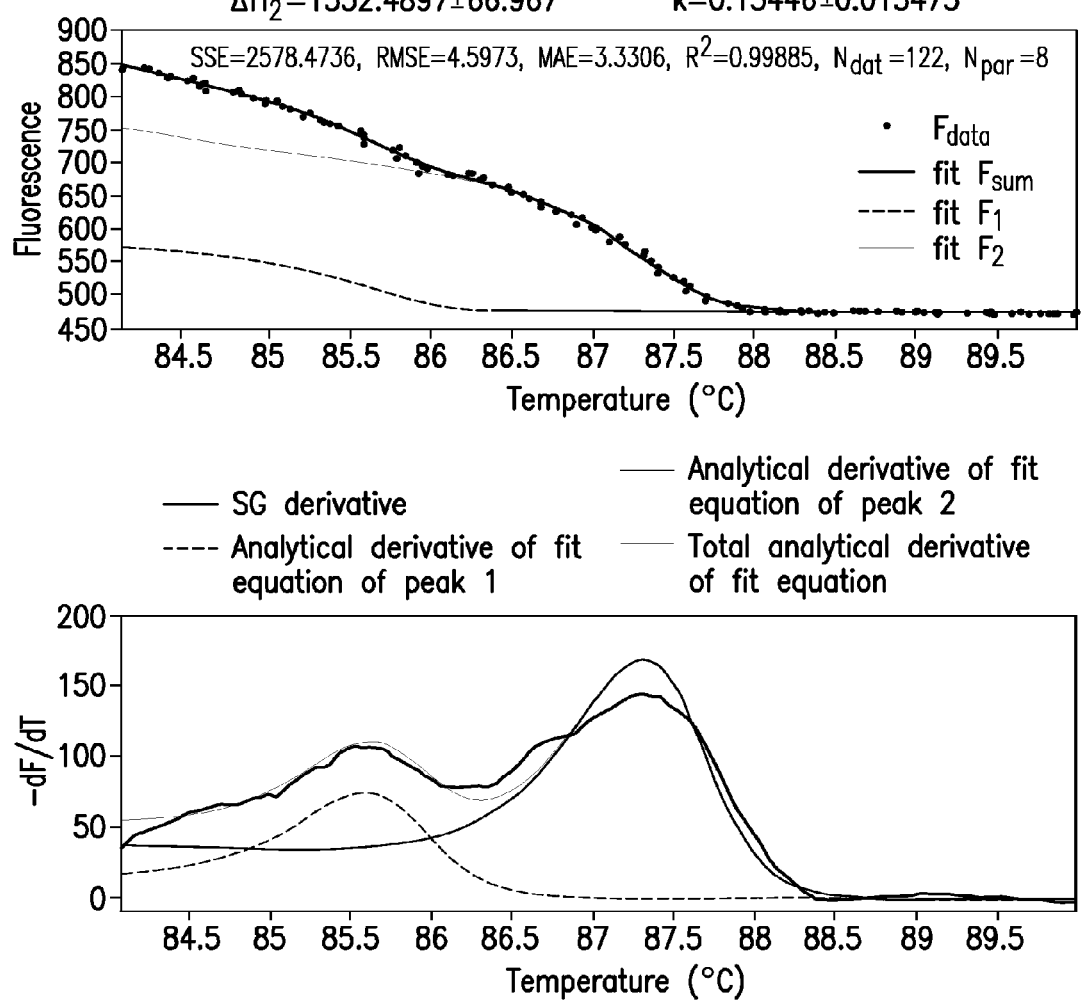

To illustrate the application of a model in accordance with one embodiment, melt curve data were generated for homozygous wild type salmonella DNA and for heterozygous mutant salmonella DNA. FIGS. 7A and 7B show the data and analysis for the homozygous wild type salmonella DNA and FIGS. 8A and 8B show the data and analysis for heterozygous mutant salmonella DNA. FIG. 7A shows that the homozygous wild type salmonella DNA is correctly fit to one peak. FIG. 7B shows that the homozygous wild type salmonella DNA is incorrectly over-fit to two peaks. Quantitatively, the $F_{ratio}$ is 2.45 in this case. This number is not much bigger than 1 and the second peak is deemed unnecessary. Thus, a single peak or feature adequately describes the shape of the melting curve for the homozygous wild type salmonella DNA. FIG. 8A shows that the heterozygous mutant salmonella DNA is inadequately fit to one peak. FIG. 8B shows that the heterozygous mutant salmonella DNA is properly fit to two peaks. Quantitatively, the $F_{ratio}$ is 106.41 in this case. This number is much bigger than 1 and the second peak is deemed necessary. Thus, a second peak or feature is needed to adequately describe the shape of the melting curve for the heterozygous mutant salmonella DNA. This process can be repeated to evaluate whether a $3^{rd}$ or $4^{th}$ feature is necessary as shown in the flowchart in FIG. 6.

The Residual Runs test can also be used to compare fit models to determine whether an added peak is necessary to describe a melt curve. The residual is the difference of the fit curve (thin line) points from the actual data (thick line). Statistically, the residual runs test can be used to test if a model fit curve adequately describes the data. A run is a consecutive series of points whose residuals are either all positive or all negative.

If the data points are randomly distributed above and below fit fluorescence line, it is possible to calculate the expected number of runs. If there are Np points above the fit curve and Np points below the curve, the total number of runs follows a normal distribution with a mean expected value of $[(2*Np*Nn)/(Np+Np)]+1$ with a standard deviation of sqrt$((2*Np*Nn*(2*Np*Nn-Np-Nn))/(((Np+Nn)^2)*(Np+Nn-1)))$. If fewer runs are obtained than the expected value then there may be some dynamic that is not being modeled for and a more complex model or added feature is required to describe the data. The p-value of the total number of runs in the distribution reflects the probability of getting as few or fewer runs as observed in this experiment for a randomly distributed set of residuals. Thus if the p value is low, it may be concluded that the model used to fit the data is inadequate.

In the top subplot of FIG. 7A, the residual fluctuates randomly about 0, indicating that a second peak is unnecessary. In contrast, the top subplot of FIG. 8A shows a stream of negative residuals followed by a stream of positive residuals (resulting in much fewer runs than expected), indicating that a second peak is necessary. In the top subplot of FIG. 8B, the residuals appear to be randomly distributed again resulting in a larger number of runs.

Figure 9:
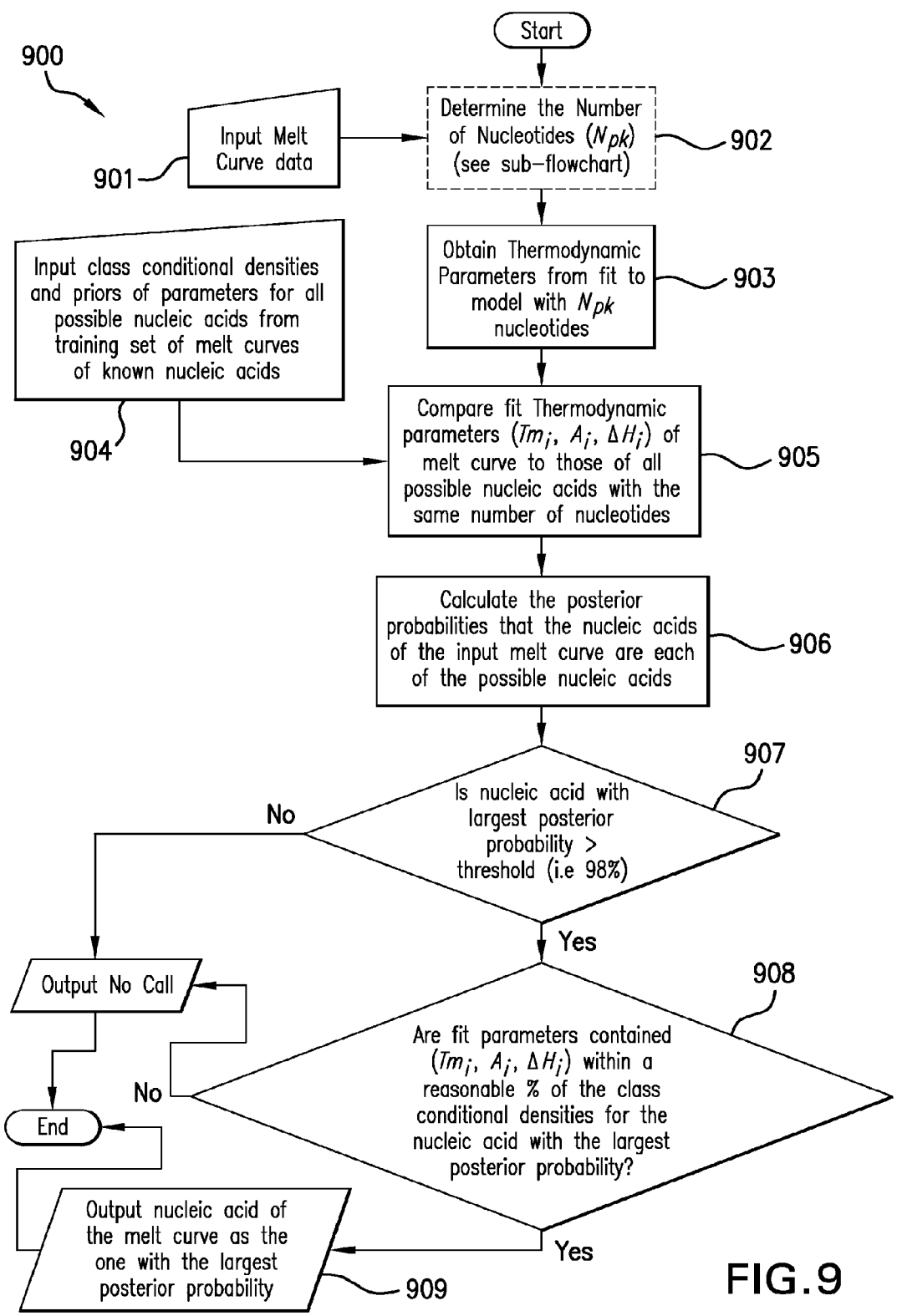
FIG. 9 illustrates a flow chart showing a method in accordance with one aspect of the present invention.

FIG. 9 illustrates a flow chart for process 900 for the analysis of denaturation data to identify a nucleic acid in a biological sample, in accordance with one embodiment. Process 900 may begin in step 901 in which the melt curve data is inputted into an appropriate programmed computer. The number of peaks or nucleotides is determined in step 902, e.g., in accordance with the flow chart illustrated in FIG. 6. Once the number of peaks or nucleotides has been determined, the thermodynamic parameters are obtained in step 903 from the fit to the model with $N_{pk}$ peaks or nucleotides. The class conditional densities and priors of parameters for all possible nucleic acids from training set of melt curves of known nucleic acids is inputted in step 904. In step 905, the fit thermodynamic parameters of a melt curve is compared to those of all possible nucleic acids. In step 906, the posterior probabilities that the nucleic acids of the input melt curve are each of the possible nucleic acids is calculated. In step 907, a query of the comparison is made as to whether the nucleic acid with the largest posterior probability is greater than a preselected threshold, e.g., 98%. If the answer is no, the process is completed with no identification of the nucleic acid. If the answer is yes, step 908 is performed. In step 908, the query is made as to whether the fit parameters are contained within a reasonable percentage of the class conditional densities for the nucleic acid with the largest posterior probability. If the answer is no, the process is completed with no identification of the nucleic acid. If the answer is yes, step 909 outputs the nucleic acid of the melt curve as the one with the largest posterior probability.

In accordance with the present invention, the derivation of −dF/dT curve is not necessary in the determination of melting temperatures and other parameters in the thermodynamic mathematical model. However, once the parameters of the mathematical model have been identified, the analytical −dF/dT of the melt curve can be obtained, as persons skilled in the art conventionally look at melt data this way. For the $i^{th}$ feature or peak, the analytical derivative of Equation 3 substituted into Equation 2 is given by:

$$dFdT(i)=\tfrac{1}{2}*A(i)*((8*\exp(dH(i)*(T-Tm(i))/R/Tm(i)/T)+1)^{(1/2)}-4*\exp(dH(i)*(T-Tm(i))/R/Tm(i)/T)-1)*(-dH(i)+k*(8*\exp(dH(i)*(T-Tm(i))/R/Tm(i)/T)+1)^{(1/2)}*R*T^2)/(8*\exp(dH(i)*(T-Tm(i))/R/Tm(i)/T)+1)^{(1/2)}/R/T^2*\exp((-T+Tm(i))*k-dH(i)*(T-Tm(i))/R/Tm(i)/T); \text{ where}$$

dFdT(i) is $$\frac{dF_i}{dT},$$

the derivative of $F_i$, Tm(i) is $T_{mi}$ (in Kelvin), dH(i) is $\Delta H_i$, A(i) is $A_i$, k is k, R is the universal gas constant, and T is the temperature shown on the x axis (in Kelvin).

The total derivative is given by:

$$\frac{dF_{sum}}{dt}=\sum_{i=1}^{N_{pk}}\frac{dF_i}{dt}.$$

It should be noted that this method of generating −dF/dT can be applied to any set of equations relating fluorescence and temperature and is not limited to Equations 1 through 3.

The advantages to obtaining the derivative of the melt curve this way include, for example, that (i) it is closer to the true derivative as there is no low pass filtering attenuating the signal (see FIG. 2), and (ii) derivatives of individual features show isolated multiple peaks when they are close together. The total derivative merges them together making them indistinguishable (see FIG. 4), which is a potential problem in using SG filters.

Thus, the invention provides methods and systems for the analysis of denaturation data in the detection of nucleic acid that contains one or more peaks or mutations. This aspect of the invention overcomes problems that arise with the use of SG filters in obtaining the negative derivative curve.

Thus, in accordance with these aspects, the present invention provides a method for identifying a nucleic acid in a sample including at least one unknown nucleic acid. In accordance with this aspect, the method comprises fitting denaturation data, including measurements of a quantifiable physical change P of the sample at a plurality of independent sample property points x, to a function P(x, Q) to determine an intrinsic physical value Q and to obtain an estimated physical change function, wherein the intrinsic physical value Q is an intrinsic physical value associated with the nucleic acid in the sample, and the quantifiable physical change P is associated with the denaturation of a nucleic acid. In one embodiment, the fitting is performed without determining the change in heat capacity of the sample.

In one embodiment, the method further comprises identifying the nucleic acid in the biological sample by comparing the intrinsic physical value Q for at least one unknown nucleic acid to an intrinsic physical value Q for a known nucleic acid. In another embodiment, the method further comprises identifying the nucleic acid in the biological sample by comparing the intrinsic physical value Q for at least one unknown nucleic acid is made to an a priori distribution of intrinsic physical values Q for a known nucleic acid to determine if the unknown nucleic acid and the known nucleic acid are identical. In another embodiment, Q is one or more fitting parameters Y, Z and W and the denaturation data is fit to one or more of these fitting parameters to determine one or more intrinsic physical values Y, Z and W. Each of the intrinsic physical values Y, Z and W is associated with a nucleic acid. For example, in one embodiment, Y is $T_m$, Z is van't Hoff enthalpy $\Delta H$ and W is amplitude A. In an additional embodiment, one or more of the intrinsic physical values Y, Z and W are determined and compared. In a further embodiment, two or more of the intrinsic physical values Y, Z and W are determined and compared. In still yet another embodiment, all of the intrinsic physical values Y, Z and W are determined and compared.

In one embodiment, the fitting step includes fitting the denaturation data to a function P(x, Q) using a computer-implemented non-linear least squares algorithm. In another embodiment, the non-linear least squares algorithm determines the value of at least one fitting parameter, and the intrinsic physical value Y is a fitting parameter whose value is determined by the non-linear least squares algorithm. In a further embodiment, the fitting step includes fitting the denaturation data to a function $P_1(x, Q)$ to obtain a first estimated physical change function in which the function $P_1(x, Q)$ describes the relationship of the quantifiable physical change of a sample containing one nucleic acid to the independent sample property x, and the method further comprises the steps of (i) fitting the denaturation data to a function $P_2(x, Q_1, Q_2)$ to obtain a second estimated physical change function, in which the function $P_2(x, Q_1, Q_2)$ describes the relationship of the quantifiable physical change of a sample containing 2 distinct nucleic acids to the independent sample property x of a sample containing 2 distinct nucleic acids, and (ii) quantifying the number of distinct nucleic acids in the sample by comparing the first and second estimated physical change functions with the denaturation data to determine if 1 or 2 distinct unknown nucleic acids are present in the sample. In another embodiment, the determining step includes determining a melting temperature $T_{m(1)}$ for a first unknown nucleic acid and determining a melting temperature $T_{m(2)}$ for a second unknown nucleic acid.

In one embodiment, the method further comprises the step of calculating the binding fraction $g_i$ of each nucleotide in the nucleic acid from the fit parameters. In another embodiment, the method further comprises the steps of calculating a derivative of the estimated physical change function dP/dx and displaying a plot of said derivative. In a further embodiment, the independent sample property x is the sample temperature T and the intrinsic physical value Y is the melting temperature $T_m$. In one embodiment, the fitting step is performed by fitting the denaturation data to an equation of the form:

$$P(T, T_m) = B + \sum_{i=1}^{n} P_i, \quad \text{(Eq. 1)}$$

wherein $$P_i = 2A_i g_i e^{[-k(T-T_{m_i})]}, \quad \text{(Eq. 2)}$$

$$g_i = 1 + \frac{1}{4e^{\left[\frac{\Delta H_i}{R^2}\left(\frac{1}{T_{m_i}} - \frac{1}{T}\right)\right]}} - \sqrt{\left(1 + \frac{1}{4e^{\left[\frac{\Delta H_i}{R^2}\left(\frac{1}{T_{m_i}} - \frac{1}{T}\right)\right]}}\right)^2 - 1}, \quad \text{(Eq. 3)}$$

and wherein

B is the baseline measurement of the quantifiable physical property in absence of the sample, $A_i$ is the amplitude of the measurement of the quantifiable physical property of the ith nucleic acid present in the sample, $\Delta H_i$ is the van't Hoff enthalpy of denaturation of the ith nucleic acid present in the sample, $T_{m(i)}$ is the melting temperature of the ith nucleic acid present in the sample, and R is the universal gas constant.

In one embodiment, the biological sample further includes a fluorescent dye, and the quantifiable physical change is fluorescence intensity for measuring the denaturation of the molecules in the sample. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In another embodiment, the quantifiable physical change is ultraviolet light for measuring the denaturation of the molecules in the sample. In further embodiment, the method further comprises the step of generating denaturation data from the sample. In one embodiment, the denaturation data is thermal melt data. In another embodiment, the unknown nucleic acid is a nucleic acid containing a single nucleotide polymorphism.

In another aspect, the invention provides methods and systems for identifying a nucleic acid in a sample including an unknown nucleic acid or for detecting a single nucleotide polymorphism in a nucleic acid in a sample including at least one unknown nucleic acid. Some nucleic acid assays require identification of a single nucleotide change where the difference in $T_m$ between the wild type and mutant nucleic acid is small, such as, for example, less than 0.25° C. This level of temperature resolution is difficult, if not impossible, in standard 96 and 384 well plates. Decreasing the area of thermal analysis can improve the spatial temperature gradient, but there is still significant noise generated from the heating device used to linearly ramp the samples during a thermal melt. It would be of great benefit to define the curve by multiple variables to increase the confidence of identifying a certain nucleic acid when comparing patient thermal melt curves to control thermal melt curves that are differentiated by small differences, such as, for example, less than 0.25° C.

In accordance with this aspect, methods are disclosed that utilize more than one variable to describe a thermal melt curve and allow a higher confidence when comparing unknown patient results to a control data set. In one embodiment, fluorescence data generated from a thermal melt curve can be defined by one or more variables, which include a slope and intercept from the upper and lower baselines, a midpoint of the transition ($T_m$) and the width of the transition (van't Hoff enthalpy, $\Delta H$). Defining a thermal melt curve by both a $T_m$ and van't Hoff enthalpy would further refine the characteristics of the control data that is to be compared to data from unknown nucleic acid in a biological sample.

By defining a control sample by a $T_m$ and van't Hoff enthalpy, $\Delta H$, in accordance with one embodiment, greater confidence in accurately identifying a nucleic acid in a biological sample is obtained. The van't Hoff enthalpy is more sensitive to data quality and is more likely to highlight differences in data sets generated by control nucleic acids with small differences in $T_m$'s. Along with the $T_m$, van't Hoff enthalpy $\Delta H$ and amplitude A, the non nucleotide specific parameter, k, derived from the melting curve can be used to further define the data and to identify the unknown nucleic acid in a biological sample.

Thus, in accordance with this aspect of the invention, methods are provided for identifying a nucleic acid in a sample including an unknown nucleic acid. According to this aspect, the method comprises fitting denaturation data, including measurements of a quantifiable physical change P of the sample at a plurality of independent sample property points x, to a function P(x, Y, Z) to determine intrinsic physical values Y and Z for the unknown nucleic acid and to obtain an estimated physical change function, wherein intrinsic physical values Y and Z are distinct intrinsic physical values associated with the nucleic acid in the sample and wherein the quantifiable physical change P is associated with denaturation of a nucleic acid. The method further comprises identifying the nucleic acid in the biological sample by comparing the intrinsic physical values Y and Z for the unknown nucleic acid to a priori distributions of the intrinsic physical values Y and Z for the known nucleic acid to determine if the unknown nucleic acid and the known nucleic acid are identical.

In one embodiment, the sample further includes a fluorescent dye for measuring the denaturation of the molecules in the sample. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In another embodiment, the quantifiable physical change is fluorescence intensity. In a further embodiment, quantifiable physical change P is ultraviolet absorbance.

In a further embodiment, x is the sample temperature T, Y is the melting temperature $T_m$ and Z is the van't Hoff enthalpy $\Delta H$. In one embodiment, the fitting step includes fitting the denaturation data to a function $P(T, T_m, \Delta H, A)$ in which A is amplitude to determine one or more nucleic acid specific parameters for the unknown nucleic acid. In another embodiment, the identifying step includes comparing one or more nucleic acid specific parameters for the unknown nucleic acid to one or more nucleic acid specific parameters for a known nucleic acid to determine if the unknown nucleic acid and the known nucleic acid are identical. In another embodiment, the method further comprises the step of calculating a derivative function dP/dx of the estimated physical change function and displaying a plot of the derivative function. In a further embodiment, the method further comprises the step of generating denaturation data from a sample including an unknown nucleic acid. In one embodiment, the denaturation data is thermal melt data.

In another embodiment, the present invention also provides a method for detecting a single nucleotide polymorphism in a nucleic acid in a sample including at least one unknown nucleic acid. According to this aspect, the method comprises fitting denaturation data to a function P(x, Y, Z) to determine intrinsic physical values Y and Z for the unknown nucleic acid and to obtain an estimated physical change function, wherein the denaturation data includes measurements of a quantifiable physical change P of the sample at a plurality of independent sample property points x, wherein intrinsic physical values Y and Z are distinct intrinsic physical values associated with the nucleic acid containing a single nucleotide polymorphism, and wherein the quantifiable physical change P is associated with denaturation of a nucleic acid. The methods further comprise detecting the presence of a single nucleotide polymorphism by comparing the intrinsic physical values Y and Z for the unknown nucleic acid to the intrinsic physical values Y and Z for a known nucleic acid to determine if the unknown nucleic acid is a single nucleotide polymorphism of the known nucleic acid. In one embodiment, the comparison of the intrinsic physical values Y and Z for at least one unknown nucleic acid is made to an a priori distribution of the intrinsic physical values Y and Z for a known nucleic acid to determine if the unknown nucleic acid and the known nucleic acid are identical.

In one embodiment, the sample further includes a fluorescent dye for measuring the denaturation of the molecules in the sample. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In another embodiment, the quantifiable physical change is fluorescence intensity. In a further embodiment, quantifiable physical change P is ultraviolet absorbance. In one embodiment, x is the sample temperature T, Y is the melting temperature $T_m$ and wherein Z is the van't Hoff enthalpy $\Delta H$. In another embodiment, the fitting step includes fitting the denaturation data to a function $P(T, T_m, \Delta H, A)$ in which A is the amplitude to determine one or more of the nucleic acid specific parameters for the unknown nucleic acid. In a further embodiment, the identifying step includes comparing the nucleic acid specific parameters for the unknown nucleic acid to the nucleic acid specific parameters for a known nucleic acid to determine if the unknown nucleic acid and the known nucleic acid are identical. In one embodiment, the method further comprises the step of calculating a derivative function dP/dx of the estimated physical change function and displaying a plot of the derivative function. In another embodiment, the method further comprises the step of generating denaturation data from a sample including an unknown nucleic acid. In one embodiment, the denaturation data is thermal melt data.

Figure 10:
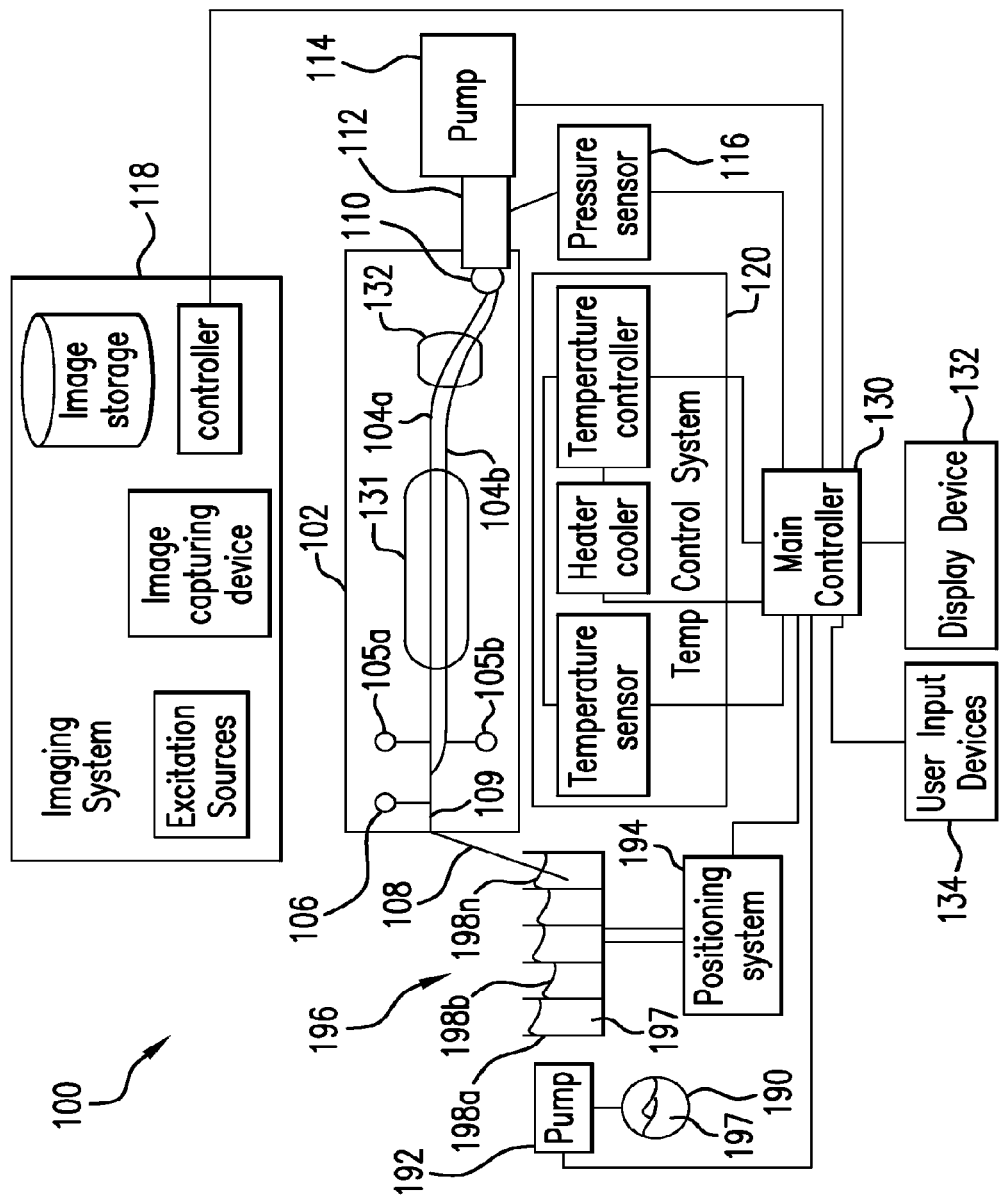
FIG. 10 illustrates a microfluidic device in accordance with some aspects of the present invention.

In accordance with other aspects, the present invention also provides a system for identifying a nucleic acid in a sample including at least one unknown nucleic acid. An example of a suitable system in accordance with some aspects of the invention is illustrated in connection with FIG. 10. As illustrated in FIG. 10, system 100 may include a microfluidic device 102. Microfluidic device 102 may include one or more microfluidic channels 104. In the examples shown, device 102 includes two microfluidic channels, channel 104a and channel 104b. Although only two channels are shown in the exemplary embodiment, it is contemplated that device 102 may have fewer than two or more than two channels. For example, in some embodiments, device 102 includes eight channels 104.

Device 102 may include two DNA processing zones, a DNA amplification zone 131 (a.k.a., PCR zone 131) and a DNA melting zone 132. A DNA sample traveling through the PCR zone 131 may undergo PCR, and a DNA sample passing through melt zone 132 may undergo high resolution thermal melting. As illustrated in FIG. 10, PCR zone 131 includes a first portion of channels 104 and melt zone 132 includes a second portion of channels 104, which is down stream from the first portion.

Device 102 may also include a sipper 108. Sipper 108 may be in the form of a hollow tube. Sipper 108 has a proximal end that is connected to an inlet 109 which inlet couples the proximal end of sipper 108 to channels 104. Device 102 may also include a common reagent well 106 which is connected to inlet 109. Device 102 may also include a locus specific reagent well 105 for each channel 104. For example, in the embodiment shown, device 102 includes a locus specific reagent well 105a, which is connected to channel 104a, and may include a locus specific reagent well 105b which is connected to channel 104b. Device 102 may also include a waste well 110 for each channel 104.

The solution that is stored in the common reagent well 106 may contain dNTPs, polymerase enzymes, salts, buffers, surface-passivating reagents, one or more non-specific fluorescent DNA detecting molecules, a fluid marker and the like. The solution that is stored in a locus specific reagent well 105 may contain PCR primers, a sequence-specific fluorescent DNA probe or marker, salts, buffers, surface-passivating reagents and the like.

In order to introduce a sample solution into the channels 104, system 100 may include a well plate 196 that includes a plurality of wells 198, at least some of which contain a sample solution (e.g., a solution containing a DNA sample). In the embodiment shown, well plate 196 is connected to a positioning system 194 which is connected to a main controller 130.

Main controller 130 may be implemented, for example, using a PXI-8105 controller which is available from National Instruments Corporation of Austin, Tex. Positioning system 194 may include a positioner (e.g., the MX80 positioner available from Parker Hannifin Corporation of PA ("Parker")) for positioning well plate 196, a stepping drive (e.g., the E-AC Microstepping Drive available from Parker) for driving the positioner, and a controller (e.g., the 6K4 controller available from Parker) for controlling the stepping drive.

To introduce a sample solution into the channels 104, the positioning system 194 is controlled to move well plate 196 such that the distal end of sipper 108 is submerged in the sample solution stored in one of the wells 198. FIG. 10 shows the distal end of 108 being submerged within the sample solution stored in well 198n.

In order to force the sample solution to move up the sipper and into the channels 104, a vacuum manifold 112 and pump 114 may be employed. The vacuum manifold 112 may be operably connected to a portion of device 102 and pump 114 may be operably connected to manifold 112. When pump 114 is activated, pump 114 creates a pressure differential (e.g., pump 114 may draw air out of a waste well 110), and this pressure differential causes the sample solution stored in well 198n to flow up sipper 108 and through inlet channel 109 into channels 104. Additionally, this causes the reagents in wells 106 and 105 to flow into a channel. Accordingly, pump 114 functions to force a sample solution and real-time PCR reagents to flow through channels 104. As illustrated in FIG. 10, melt zone 132 is located downstream from PCR zone 131. Thus, a sample solution will flow first through the PCR zone and then through the melting zone.

Referring back to well plate 196, well plate 196 may include a buffer solution well 198a. In one embodiment, buffer solution well 198a holds a buffer solution 197. Buffer solution 197 may comprise a conventional PCR buffer, such as a conventional real-time (RT) PCR buffer. Conventional PCR buffers are available from a number of suppliers, including: Bio-Rad Laboratories, Inc., Applied Biosystems, Roche Diagnostics, and others.

In order to achieve PCR for a DNA sample flowing through the PCR zone 131, the temperature of the sample must be cycled, as is well known in the art. Accordingly, in some embodiments, system 100 includes a temperature control system 120. The temperature control system 120 may include a temperature sensor, a heater/cooler, and a temperature controller. In some embodiments, a temperature control system 120 is interfaced with main controller 130 so that main controller 130 can control the temperature of the samples flowing through the PCR zone and the melting zone. Main controller 130 may be connected to a display device for displaying a graphical user interface. Main controller 130 may also be connected to user input devices 134, which allow a user to input data and commands into main controller 130.

To monitor the PCR process and the melting process that occur in PCR zone 131 and melt zone 132, respectively, system 100 may include an imaging system 118. Imaging system 118 may include an excitation source, an image capturing device, a controller, and an image storage unit. Other aspects of a suitable system in accordance with some aspects of the invention are disclosed in U.S. patent application Ser. No. 11/770,869, incorporated herein by reference in its entirety.

The system 100 further includes an appropriately controllable computer in communication with the user input devices 134, display device 132 and the main controller 130. The computer receives information from, among many sources, the imaging system 118 and temperature control system 120 and enables the identification of a nucleic acid in a sample including an unknown nucleic acid in accordance with some aspects of the invention.

According to this aspect, the system for identifying a nucleic acid in a sample including at least one unknown nucleic acid comprises a fitting module capable of fitting denaturation data received from, among other sources, the imaging system and temperature control system including measurements of a quantifiable physical change P of the sample at a plurality of independent sample property points x to a function P(x, Q) to determine intrinsic physical value Q for the unknown nucleic acid, wherein Q is a distinct intrinsic physical value associated with the nucleic acid in the sample, and wherein the quantifiable physical change P is associated with denaturation of a nucleic acid. In accordance with one embodiment, the fitting module comprises an appropriately programmed computer or software stored on a computer readable medium (e.g., a non-volatile storage device or other storage device), where the software is configured such that when executed by a computer, the software enables the computer to fit denaturation data to a function P(x, Q) to determine intrinsic physical value Q.

The system in accordance with some aspects of the invention further comprises an identification module capable of identifying the nucleic acid in the biological sample by comparing the intrinsic physical value Q value for the unknown nucleic acid to the intrinsic physical value Q value for a known nucleic acid to determine if the unknown nucleic acid and the known nucleic acid are identical. In accordance with one embodiment, the identification module comprises an appropriately programmed computer or software stored on a computer readable medium, where the software is configured such that when executed by a computer, the software enables the computer to compare the intrinsic physical value Q value for the unknown nucleic acid to the intrinsic physical value Q value for a known nucleic acid to determine if the unknown nucleic acid is a single nucleotide polymorphism of the known nucleic.

In one embodiment, Q is one or more fitting parameters Y, Z and W and the denaturation data is fit to one or more of these fitting parameters to determine one or more intrinsic physical values Y, Z and W. In another embodiment, one or more of the intrinsic physical values Y, Z and W are determined and compared. In an additional embodiment, two or more of the intrinsic physical values Y, Z and W are determined and compared. In a further embodiment, all of the intrinsic physical values Y, Z and W are determined and compared. In one embodiment, x is the sample temperature T, Y is the melting temperature $T_m$, Z is the van't Hoff enthalpy $\Delta H$ and W is the amplitude A. In some embodiments, Y and Z are determined and compared in the method according to the invention.

In one embodiment, the biological sample further includes a fluorescent dye, and the quantifiable physical change is fluorescence intensity for measuring the denaturation of the molecules in the sample. Suitable fluorescent dyes for detecting denaturation of molecules are well known in the art and include those described herein, such as the double-strand specific dyes of the SYBR Green family of dyes and LCGreen Plus. Any suitable fluorescent dye can be used in the methods of the invention. In a further embodiment, the quantifiable physical change is fluorescence intensity.

In one embodiment, the fitting module is further capable of fitting the denaturation data to a function $P(T, T_m, \Delta H, A)$ in which A is amplitude to determine one or more nucleic acid specific parameters for the unknown nucleic acid. In another embodiment, the identifying module is further capable of comparing the nucleic acid specific parameters for the unknown nucleic acid to the nucleic acid specific parameters for a known nucleic acid to determine if the unknown nucleic acid and the known nucleic acid are identical. In a further embodiment, the system further comprises a single-nucleotide-polymorphism detection module capable of comparing intrinsic physical values Y and Z for the unknown nucleic acid to a priori distributions of the intrinsic physical values Y and Z for a known nucleic acid to determine if the unknown nucleic acid is a single nucleotide polymorphism of the known nucleic acid. In one embodiment, the system further comprises a generating unit capable of generating denaturation data from a sample. In one embodiment, the generating unit comprises an appropriately programmed computer or software stored on a computer readable medium, where the software is configured such that when executed by a computer, the software enables the computer to generate denaturation data including measurements of a quantifiable physical change P of the sample at a plurality of independent sample property points x for a sample. In one embodiment, the denaturation data is thermal melt data.

In one embodiment, the fitting module is a computer containing instructions for performing a non-linear least squares algorithm. In another embodiment, the independent sample property x is the sample temperature T. In a further embodiment, the intrinsic physical value Y is the melting temperature $T_m$. In one embodiment, the computer containing instructions for performing a non-linear least squares algorithm further contains instructions for fitting the denaturation data to a function as described herein.

In one embodiment, the fitting module includes a computer or software stored on a computer readable medium containing instructions for performing a non-linear least squares algorithm to determine the value of at least one fitting parameter, in which the melting temperature $T_m$ is a fitting parameter whose value is capable of being determined by the non-linear least squares algorithm. In another embodiment, the system further comprises a generating unit capable of generating denaturation data from the sample. In one embodiment, the denaturation data is thermal melt data. The generating unit is as described herein. In another embodiment, the single-nucleotide-polymorphism module is further capable of comparing nucleic acid specific parameters for the unknown nucleic acid to the nucleic acid specific parameters for a known nucleic acid to determine if the unknown nucleic acid is a single nucleotide polymorphism of the known nucleic acid.

In other aspects, the present invention further provides a method for quantifying the number of distinct nucleic acids in a sample, wherein the sample includes at least one nucleic acid. This method comprises fitting denaturation data, including measurements of a quantifiable physical change P of the sample at a plurality of independent sample property points x, to a function $P_n(x)$ to obtain a first estimated physical change function, wherein the function $P_n(x)$ describes the relationship of the quantifiable physical change of a sample containing n distinct nucleic acids to an independent sample property x of a sample containing n distinct nucleic acids, and the quantifiable physical change P is associated with the denaturation of a nucleic acid. The method further comprises fitting the denaturation data to a function $P_{n+1}(x)$ to obtain a second estimated physical change function, wherein said function $P_{n+1}(x)$ describes the relationship of the quantifiable physical change of a sample containing n+1 distinct nucleic acids to an independent sample property x of a sample containing n+1 distinct nucleic acids. The method also comprises quantifying the number of distinct nucleic acids in the sample by comparing the first and second estimated physical change functions with the denaturation data to determine if n or n+1 different nucleic acids are present in the sample.

In one embodiment, the first fitting step includes determining the intrinsic physical value $Q_1$ for at least one of the nucleic acids present in the sample, and wherein said second fitting step includes determining an intrinsic physical value $Q_2$ for at least one of the nucleic acids in the sample. In another embodiment, the first fitting step includes fitting the denaturation data to a function $P_n(x)$ using a computer-implemented fitting algorithm, and the second fitting step includes fitting the denaturation data to a function $P_{n+1}(x)$ using a computer-implemented fitting algorithm. In a further embodiment, the independent sample property is the sample temperature T. In one embodiment, the computer-implemented fitting algorithms are non-linear least squares algorithms. In another embodiment, the non-linear least squares algorithm determines the value of at least one fitting parameter, in which the melting temperature $T_m$ of at least one nucleic acid is a fitting parameter whose value is determined by the non-linear least squares algorithm. In a further embodiment, the method further comprises the step of generating denaturation data from the sample. In one embodiment, the denaturation data is thermal melt data.

The present invention also provides a system for quantifying the number of distinct nucleic acids in a sample, said sample including at least one nucleic acid. This system comprises a fitting module capable of fitting denaturation data including measurements of a quantifiable physical change P of the sample at a plurality of independent sample property points x to a function $P_n(x)$ to obtain an n nucleic acid estimated physical change function, wherein said function $P_n(x)$ describes the relationship of the quantifiable physical change of a sample containing n distinct nucleic acids to the independent sample property of a sample containing n distinct nucleic acids, and the quantifiable physical change is associated with the denaturation of a nucleic acid. The system further comprises a quantification module capable of quantifying the number of distinct nucleic acids in the sample by comparing an n nucleic acid physical change function and an n+1 nucleic acid physical change function with the denaturation data to determine if n or n+1 different nucleic acids are present in the sample.

In accordance with one embodiment of this aspect of the invention, the fitting module comprises an appropriately programmed computer or software stored on a computer readable medium, where the software is configured such that when executed by a computer, the software enables the computer to fit denaturation data including measurements of a quantifiable physical change P of the sample at a plurality of independent sample property points x to a function $P_n(x)$ to obtain an n nucleic acid estimated physical change function, wherein said function $P_n(x)$ describes the relationship of the quantifiable physical change of a sample containing n distinct nucleic acids to the independent sample property of a sample containing n distinct nucleic acids, and the quantifiable physical change is associated with the denaturation of a nucleic acid. In another embodiment, the quantification module is an appropriately programmed computer or software stored on a computer readable medium, where the software is configured such that when executed by a computer, the software enables the computer to determine if n or n+1 different nucleic acids are present in the sample.

In one embodiment, the independent sample property x is the sample temperature T. In another embodiment, the fitting module is capable of estimating the melting temperature $T_m$ for at least one of the nucleic acids present in the sample, in which the second fitting step includes estimating the melting temperature $T_m$ for at least one of the nucleic acids in the sample. In a further embodiment, the fitting module is a computer containing instructions for fitting the denaturation data to a function $P_n(T)$ via a non-linear least squares algorithm. In one embodiment, the non-linear least squares algorithm is capable of determining the value of at least one fitting parameter, in which the melting temperature $T_m$ of at least one nucleic acid is a fitting parameter whose value is capable of being determined by the non-linear least squares algorithm. In another embodiment, the system further comprises a generating unit capable of generating denaturation data from the sample. In one embodiment, the denaturation data is thermal melt data. The generating unit is as described herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for identifying one or more nucleic acids in a sample including at least one unknown nucleic acid, said method comprising the steps of:
    (a) forming a nucleic acid denaturation function $P(x, Q_1, \ldots, Q_i)$ as a mathematical representation including parameters $Q_1, \ldots, Q_i$ defining intrinsic physical values characterizing the nucleic acids in the sample;
    (b) fitting measured denaturation data including a measured quantifiable physical change P of the sample at a plurality of independent sample property points x to the nucleic acid denaturation function $P(x, Q_1, \ldots, Q_i)$ to determine the intrinsic physical values $Q_1, \ldots, Q_i$ each of which is associated with one of the nucleic acids; and
    (c) identifying the nucleic acid in the biological sample by comparing the determined intrinsic physical value $Q_i$ for each unknown nucleic acid to an intrinsic physical value $Q_i$ for a known nucleic acid.

2. The method according to claim 1, wherein the mathematical representation of the nucleic acid denaturation function $P(x, Q_1, \ldots, Q_i)$ is a series with the number of terms being equal to the number of nucleic acids in the sample, each term in the series characterizing one of the one or more nucleic acids in the sample.

3. The method according to claim 1, wherein the comparison of the intrinsic physical value $Q_i$ for one or more unknown nucleic acid is made to an a priori distribution of intrinsic physical value $Q_i$ for a known nucleic acid to determine if the unknown nucleic acid and the known nucleic acid are identical.

4. The method according to claim 1, wherein values $Q_1, \ldots, Q_i$ are fitting parameters Y, Z and W and the measured denaturation data is fit to one or more of these fitting parameters to determine one or more intrinsic physical values Y, Z and W.

5. The method according to claim 4, wherein one or more of the intrinsic physical values Y, Z and W are determined and compared to corresponding values for known nucleic acids.

6. The method according to claim 5, wherein x is the sample temperature T, Y is the melting temperature $T_m$, Z is the van't Hoff enthalpy $\Delta H$ and W is the amplitude A.

7. The method according to claim 1, wherein said sample further includes a fluorescent dye, and wherein said quantifiable physical change P is fluorescence intensity.

8. The method according to claim 1, wherein said quantifiable physical change P is ultraviolet absorbance.

9. The method according to claim 1, wherein said fitting step includes fitting the measured denaturation data to the function $P(x, Q_1, \ldots, Q_i)$ using a computer-implemented non-linear least squares algorithm.

10. The method according to claim 9, wherein said non-linear least squares algorithm determines the value of at least one fitting parameter, and wherein the intrinsic physical values $Q_1, \ldots, Q_i$ are fitting parameter whose values are determined by the non-linear least squares algorithm.

11. The method according to claim 1, wherein said fitting step includes fitting the denaturation data to a function $P_1(x, Q_1)$ to obtain a first estimated physical change function, wherein said function $P_1(x, Q_1)$ describes the relationship of the quantifiable physical change of a sample containing one nucleic acid to the independent sample property x, and further comprising the steps of fitting the denaturation data to a function $P_2(x, Q_1, Q_2)$ to obtain a second estimated physical change function, wherein said function $P_2(x, Q_1, Q_2)$ describes the relationship of the quantifiable physical change of a sample containing two distinct nucleic acids to the independent sample property x of a sample containing two distinct nucleic acids; and quantifying the number of distinct nucleic acids in the sample by comparing the first and second estimated physical change functions with the denaturation data to determine if one or two distinct unknown nucleic acids are present in the sample.

12. The method according to claim 11, wherein said determining step includes determining a melting temperature $T_{m(1)}$ for a first unknown nucleic acid and determining a melting temperature $T_{m(2)}$ for a second unknown nucleic acid.

13. The method according to claim 1, further comprising the step of calculating a binding fraction gi of each nucleotide in the nucleic acid from the fit parameters.

14. The method according to claim 1, further comprising the steps of calculating a derivative of the estimated physical change function $dP(x, Q_1, \ldots, Q_i)/dx$ and displaying a plot of said derivative.

15. The method according to claim 2, wherein said fitting step is performed by fitting the denaturation data to an equation of the form $$P(T, T_m) = B + \sum_{i=1} P_i \quad \text{(Eq. 1)}$$

$$P_i = 2A_i g_i e^{[-k(i(T-T_{m_i}))]} \quad \text{(Eq. 2)}$$

wherein $$g_i = 1 + \frac{1}{4e^{\left[\frac{\Delta H_i}{R}\left(\frac{1}{T_{m_i}} - \frac{1}{T}\right)\right]}} - \sqrt{\left(1 + \frac{1}{4e^{\left[\frac{\Delta H_i}{R}\left(\frac{1}{T_{m_i}} - \frac{1}{T}\right)\right]}}\right)^2 - 1} \quad \text{(Eq. 3)}$$

and wherein B is the baseline measurement of the quantifiable physical property in absence of the sample, $A_1$ is the amplitude of the measurement of the quantifiable physical property of the ith nucleic acid present in the sample, $\Delta H_i$ is the van't Hoff enthalpy of denaturation of the ith nucleic acid present in the sample, $T_{m(i)}$ is the melting temperature of the ith nucleic acid present in the sample, and R is the universal gas constant.

16. The method according to claim 1, further comprising the step of generating the measured denaturation data from the sample, wherein said measured denaturation data is thermal melt data.

17. The method of claim 1, wherein the unknown nucleic acid is a nucleic acid containing a single nucleotide polymorphism.

18. A system for identifying one or more nucleic acids in a sample containing one or more unknown nucleic acid, the system comprising:

(a) a representation module to form a nucleic acid denaturation function $P(x, Q_1, \ldots, Q_i)$ as a mathematical representation including parameters $Q_1, \ldots, Q_i$ defining intrinsic physical values characterizing each of the one or more nucleic acids in the sample;

(b) a fitting module to fit measured denaturation data including a measured quantifiable physical change P of the sample at a plurality of independent sample property points x to the nucleic acid denaturation function $P(x, Q_1, \ldots, Q_i)$ to determine the intrinsic physical values $Q_1, \ldots, Q_i$ each of which is associated with one of the nucleic acids in the sample; and (c) an identification module to identify the nucleic acids in the biological sample by comparing the intrinsic physical values $Q_i$ for each unknown nucleic acid in the sample to an intrinsic physical value $Q_i$ for a known nucleic acid.

19. The system of claim 18, wherein the mathematical representation of the nucleic acid denaturation function $P(x, Q_1, \ldots, Q_i)$ is a series with the number of terms being equal to the number of nucleic acids in the sample, each term in the series characterizing one of the one or more nucleic acids in the sample.

20. The system according to claim 18, wherein $Q_1, \ldots, Q_i$ are fitting parameters Y, Z and W and the fitting module fits the denaturation data to one or more of these fitting parameters to determine one or more intrinsic physical values Y, Z and W.

21. The system according to claim 20, wherein one or more of the intrinsic physical values Y, Z and W are determined and compared to corresponding intrinsic physical values for known nucleic acids.

22. The system according to claim 20, wherein x is the sample temperature T, Y is the melting temperature $T_m$, Z is the van't Hoff enthalpy $\Delta H$ and W is the amplitude A.

23. The system according to claim 18, wherein said fitting module is a computer containing instructions for performing a non-linear least squares algorithm.

24. The system according to claim 19, wherein said computer containing instructions for performing a non-linear least squares algorithm further contains instructions for fitting the denaturation data to the nucleic acid denaturation function of the form $$P(T, T_m) = B + \sum_{i=1}^{n} P_i, \quad \text{(Eq. 1)}$$

wherein $$P_i = 2A_i g_i e^{[-k(T-T_{m_i})]}, \quad \text{(Eq. 2)}$$

$$g_i = 1 + \frac{1}{4e^{\left[\frac{\Delta H_i}{R}\left(\frac{1}{T_{m_i}} - \frac{1}{T}\right)\right]}} - \sqrt{\left(1 + \frac{1}{4e^{\left[\frac{\Delta H_i}{R}\left(\frac{1}{T_{m_i}} - \frac{1}{T}\right)\right]}}\right)^2 - 1}, \quad \text{(Eq. 3)}$$

and wherein B is the baseline measurement of the quantifiable physical property in absence of the sample, Ai is the amplitude of the measurement of the quantifiable physical property, $\Delta H_i$ is the van't Hoff enthalpy of denaturation of the ith nucleic acid present in the sample, $T_{m(i)}$ is the melting temperature of the ith nucleic acid present in the sample, and R is the universal gas constant.

25. The system according to claim 22, wherein said fitting module includes a computer containing instructions for performing a non-linear least squares algorithm to determine the value of at least one fitting parameter, and where the melting temperature $T_m$ is a fitting parameter whose value is capable of being determined by the non-linear least squares algorithm.

* * * * *